US008011229B2

(12) United States Patent
Lieberman et al.

(10) Patent No.: US 8,011,229 B2
(45) Date of Patent: Sep. 6, 2011

(54) DETERMINING POSTURAL STABILITY

(75) Inventors: Erez Lieberman, Cambridge, MA (US); Katharine E. Forth, Houston, TX (US); William H. Paloski, League City, TX (US)

(73) Assignees: Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 15 days.

(21) Appl. No.: 12/323,912

(22) Filed: Nov. 26, 2008

(65) Prior Publication Data

US 2009/0260426 A1 Oct. 22, 2009

Related U.S. Application Data

(60) Provisional application No. 60/990,817, filed on Nov. 28, 2007.

(51) Int. Cl.
*G01M 1/00* (2006.01)

(52) U.S. Cl. .................................... 73/65.01

(58) Field of Classification Search ....... 73/65.01–65.09
See application file for complete search history.

(56) References Cited

U.S. PATENT DOCUMENTS

| | | | |
|---|---|---|---|
| 5,209,240 A | 5/1993 | Jain et al. | |
| 5,263,491 A * | 11/1993 | Thornton | 600/587 |
| 5,388,591 A | 2/1995 | De Luca et al. | |
| 5,790,256 A | 8/1998 | Brown et al. | |
| 5,919,149 A | 7/1999 | Allum | |
| 5,987,982 A * | 11/1999 | Wenman et al. | 73/379.08 |
| 6,063,046 A | 5/2000 | Allum | |
| 6,165,143 A | 12/2000 | van Lummel | |
| 6,273,863 B1 | 8/2001 | Avni et al. | |
| 6,280,392 B1 * | 8/2001 | Yoshimi et al. | 600/534 |
| 6,741,911 B2 * | 5/2004 | Simmons | 700/245 |
| 7,141,026 B2 * | 11/2006 | Aminian et al. | 600/595 |
| 2004/0173220 A1 | 9/2004 | Harry et al. | |
| 2006/0194178 A1 | 8/2006 | Goldstein | |
| 2008/0078030 A1 * | 4/2008 | Lee et al. | 5/616 |
| 2008/0108913 A1 * | 5/2008 | Lengsfeld et al. | 600/595 |
| 2009/0137933 A1 * | 5/2009 | Lieberman et al. | 600/595 |
| 2009/0187129 A1 * | 7/2009 | Ben-Galim et al. | 602/18 |
| 2009/0210093 A1 * | 8/2009 | Jacobsen et al. | 700/260 |

(Continued)

FOREIGN PATENT DOCUMENTS

AU 199461875 11/1993

(Continued)

OTHER PUBLICATIONS

Ishida, A and Miyazaki, S., Maximum Likelihood Identification of a Posture Control System, *IEEE Transactions of Biomedical Engineering*, vol. 34 (1987), pp. 1-5.

(Continued)

*Primary Examiner* — Max Noori
(74) *Attorney, Agent, or Firm* — Proskauer Rose LLP

(57) ABSTRACT

A method for determining postural stability of a person can include acquiring a plurality of pressure data points over a period of time from at least one pressure sensor. The method can also include the step of identifying a postural state for each pressure data point to generate a plurality of postural states. The method can include the step of determining a postural state of the person at a point in time based on at least the plurality of postural states.

23 Claims, 17 Drawing Sheets

U.S. PATENT DOCUMENTS

2009/0247909 A1* 10/2009 Mukumoto ............... 600/592

FOREIGN PATENT DOCUMENTS

| CN | 1 7718 86 | 5/2006 |
|---|---|---|
| FR | 2 873 917 | 2/2006 |
| KR | 2001 011583 | 7/1999 |
| KR | 100599501 | 7/2006 |
| RU | 2 185 094 | 7/2002 |
| RU | 2 257 143 | 7/2005 |
| RU | 2004 106 030 | 8/2005 |
| RU | 2 266 705 | 12/2005 |
| SU | 1126285 | 11/1984 |
| SU | 1463220 | 3/1989 |
| TW | 240624 | 10/2005 |
| WO | 95/27185 | 10/1995 |
| WO | 97/40471 | 10/1997 |
| WO | 01/95980 | 12/2001 |
| WO | 2007/094598 | 8/2007 |
| WO | 2008/058048 | 5/2008 |

OTHER PUBLICATIONS

Nashner, L.M. and Peters, J.F., Dynamic Posturography in the Diagnosis and Management of Dizziness and Balance Disorders, *Neurologics Clinics*, vol. 8, No. 2 (May 1990), pp. 331-349.

Duarte, M. et al., Stabilographic Analysis of Unconstrained Standing, *Ergonomics*, vol. 43, No. 11 (2000) pp. 1824-1839.

Samuel, Eugenie, "Walking on Shaky Shoes", *New Scientist* (Nov. 2, 2002) p. 22.

Loram, I.D. and Lakie, M., Human Balancing of an Inverted Pendulum: Position Control by Small, Ballistic-Like, Throw and Catch Movements, *Journal of Physiology*, vol. 540.3 (2002), pp. 1111-1124.

Priplata, Atilla et al., "Noise-Enhanced Human Balance Control" *Physical Review Letters*, vol. 89, No. 23 (Dec. 2, 2002) pp. 238101-238104 to 238101-238104.

Moss, Frank et al. "Balancing the Unbalanced" *Nature*, vol. 425 (2003) pp. 911-912.

Tossavainen et al., "Development of Virtual Reality Stimuli for Force Platform Posturography", *International Journal of Medical Informatics*, vol. 70, No. 2-3 (Jul. 1, 2003) pp. 277-283.

Jeka, J et al., Controlling Human Upright Posture: Velocity Information Is More Accurate Than Position or Acceleration, *Journal of Neurophysiology*, vol. 92(4) (2004), pp. 2368-2379.

Tsuruoka, Y. and Shibasaki, R., Spectral Analysis in Walking Balance by Elderly Subjects, *Proceedings of the 28th IEEE EMBS Annual International Conference*, (2006) pp. 5420-5423.

Bamberg, Stacy et al., "Development of a Quantitative In-Shoe Measurement System for Assessing Balance: Sixteen-Sensor Insoles", *Proceedings of the 28th IEEE EMBS Annual International Conference*, (2006) pp. 6041-6044.

Forth, K.E. et al., Age Associated Differences in Postural Equilibrium Control: A Comparison Between EQscore and Minimum Time to Contact (TTC(min)), *Gait and Posture*, vol. 25(1) (2007), pp. 56-62.

Rasku et al., "Recognition of Balance Signals Between Healthy Subjects and Otoneurological Patients With Hidden Markov Models", *Biomedical Signal Processing and Control*, vol. 2, No. 1 (Jan. 2, 2007), pp. 1-8.

International Search Report and Written Opinion for International Patent Application No. PCT/US2008/084864 dated Oct. 5, 2009.

* cited by examiner

DETERMINING POSTURAL STABILITY

CROSS-REFERENCE TO RELATED APPLICATION

This application claims the benefit of and priority to U.S. provisional patent Application No. 60/990,817 filed Nov. 28, 2007, which is owned by the assignee of the instant application and the disclosure of which is incorporated herein by reference in its entirety.

GOVERNMENT SUPPORT

This invention was made with government support under grant number EO01001 awarded by NASA. The government has certain rights in this invention.

FIELD OF THE INVENTION

The invention generally relates to determining postural stability. Specifically, the invention relates to a method and apparatus/system for determining a subject's postural state.

BACKGROUND OF THE INVENTION

Poor posture can lead to postural instability (e.g., lack of balance), for example, as a person ages and/or when the person is injured. Other causes for postural instability can include the return of a person from a zero gravity environment, a lack of exercise, and/or an injury. Detection and correction of a subject's (e.g., a person's) postural instability can be challenging outside of a lab environment and/or on a real-time basis.

SUMMARY OF THE INVENTION

In one aspect, the invention features a method for determining postural stability of a person and can include the step of acquiring a plurality of pressure data points (e.g., pressure information) over a period of time from at least one pressure sensor. The method can include the step of identifying a postural state for each pressure data point to generate a plurality of postural states. The method can also include the step of determining a postural state of the person at a point in time based on at least the plurality of postural states.

In another aspect, the invention features a method for determining a postural stability (e.g., of a person). The method can include the step of acquiring at least a first pressure data point and a second pressure data point from at least one pressure sensor. The method can also include the step of identifying a first postural state and a second postural state based on the first and second pressure data points. The method can also include the step of determining a postural state (e.g., postural state of the person) at a point in time based on at least the first postural state and the second postural state.

In yet another aspect, the invention features a system for determining a postural stability of a person. The system can include at least one pressure sensor coupled to the person that acquires a plurality of pressure data points over a period of time. The system can also include a means for identifying a postural state for each pressure data point and a means for generating a plurality of postural states of the person over the period of time. The system can also include a means for determining a postural state of the person at a point in time based on the plurality of postural states.

In one aspect, the invention features a method to determine postural stability. The method can include receiving pressure information (e.g., pressure data points) from a sensor coupled to a load bearing structure. A current postural state for a structure associated with the load bearing structure can be determined based on the received pressure information. A next postural state of the structure can be determined based on a range of postural stability, the current postural state, a probability of the next postural state or any combination thereof.

In another aspect, the invention features a computer program product to determine postural stability. The computer program product can be tangibly embodied in a computer or a removable storage device. The computer program product can include instructions being operable to cause a data processing apparatus to receive pressure information from a sensor coupled to a load bearing structure. A current postural state for a structure associated with the load bearing structure can be determined based on the received pressure information. A next postural state of the structure can be determined based on a range of postural stability, the current postural state, a probability of the next postural state or any combination thereof.

In yet another aspect, the invention features a system for determining postural stability. The system includes a stability processing module. The stability processing module can be configured to receive pressure information from a sensor coupled to a load bearing structure. The stability processing module can be further configured to determine a current postural state for a structure associated with the load bearing structure based on the received pressure information. The stability processing module can be further configured to determine a next postural state of the structure based on a range of postural stability, the current postural state, a probability of the next postural state, or any combination thereof.

In another aspect, the invention features a system to determine postural stability. The system includes a means for receiving pressure information from a sensor coupled to a load bearing structure. The system further includes a means for determining a current postural state for a structure associated with the load bearing structure based on the received pressure information. The system further includes a means for determining a next postural state of the structure based on a range of postural stability, the current postural state, a probability of the next postural state, or any combination thereof.

In other examples, any of the aspects above, or any apparatus or method described herein, can include one or more of the following features.

A range of postural stability states can include or be determined by the plurality of pressure data points. In some embodiments, a postural state of the person is at least one of a static postural state or a dynamic postural state. A dynamic postural state can be defined as when the person is moving from a first static postural state to a second static postural state. A person can be identified or determined to be posturally stable or posturally unstable based on a number of times the person is in the dynamic postural state.

In some embodiments, a plurality of postural states follows a punctuated equilibrium where a continuous series of static postural states defines an equilibrium. In some embodiments, a person can be identified or determined to be posturally stable or unstable based on a number of distinct equilibria.

Determining a postural state of the person at the point in time can be based on, at least, a probability of transitioning between the static postural state and the dynamic postural state. In some embodiments, the probability of transitioning between the static postural state and the dynamic postural state can be calculated based on the plurality of postural states of the person over the period of time (e.g., by looking at the trend of how the plurality of postural states varies between, for example, static or dynamic postural states).

In some embodiments, an acceleration of the person can be acquired over the period of time. A location of the person can also be determined/acquired by a sensor (e.g., GPS location device).

In some embodiments, a postural state of a person at a point in time can be determined by using a machine learning technique (e.g., a Hidden Markov Model or Bayesian segmentation) on the plurality of pressure data points to generate the plurality of postural states. A postural state of a person at a point in time can be determined by using a Hidden Markov Model on the plurality of pressure data points to determine a postural state of a person at a point in time (e.g., based on pressure points and information acquired to generate a plurality of postural states). A Hidden Markov Model can be used on the plurality of pressure data points to, for example, project or calculate a postural state of a person at a later point in time. A postural state of a person at a point in time (e.g., a future/subsequent postural state) can be determined by applying Bayesian segmentation to the plurality of pressure data points (e.g., which can be used to generate the plurality of postural states).

In some embodiments, a plurality of pressure data points are acquired from at least one pressure sensor on a shoe worn by the person, a sock, a sole insert, a cane, a crutch, a walker, a walking aid used by a person, a prosthetic leg, a robotic leg, a vehicle, or an axle connected to at least one wheel.

Each of the plurality of pressure data points can reflect a location of a center of mass or a center of gravity/force of the person at a point in time. A change of the location of the center of mass of the person can be determined over the period of time. In some embodiments, identifying a pressure data point as corresponding to a static or dynamic postural state can be done by grouping a selected set of the plurality of pressure data points as corresponding to a static postural state, based on the location of the center of mass/gravity/force of the person of each of the plurality of pressure data points.

In some embodiments, determining a postural state of a person at a point in time can include determining a subsequent postural state of the person. A postural state of the person can be determined either in real time or at a later point in time after the pressure points/postural states have been acquired/determined/identified. For example, as the plurality of pressure data points are being acquired, a postural state of a person at a point in time (e.g., a subsequent postural state of the person) can be determined in real time, based on the plurality of pressure data points. In some embodiments, a postural state of a person at a point in time (e.g., a current postural state or a subsequent postural state of the person) can be determined based on the plurality of pressure data points which were acquired during a previous period in time (e.g., a current or subsequent postural state of a person can be determined based on pressure data points/postural states that were acquired/determined previously, such as, for example, 6 months ago).

In some embodiments, a postural state of a person at a point in time can include determining a subsequent postural state of the person based a probability of transitioning between the static postural state and the dynamic postural state. The probability of transitioning between the static postural state and the dynamic postural state can be based, at least in part, by the identified first postural state and the identified second postural state.

In some embodiments, a person can be identified (e.g., determined to be) posturally stable or posturally unstable based on at least an identified first postural state and an identified second postural state (e.g., identified from pressure data points).

In some embodiments, a Hidden Markov Model calculation is utilized to determine a next postural state. Probabilities of transitioning between a plurality of stable and unstable postural states can be utilized to determine the next postural state. In some embodiments, the probabilities of transitioning between stable and unstable postural states are determined. The probabilities of transitioning between stable and unstable postural states can be determined based on the range of postural stability.

In some embodiments, the received pressure information is stored. The range of postural stability for a structure can be determined based on the stored pressure information. In some embodiments, the current postural state is stored. A statistic, a score, and/or a simulation is determined based on the stored postural state. A message is transmitted to a postural analysis module using a network. The message includes the statistic, the score, the simulation, the current postural state, the next postural state, and/or the range of postural stability.

In some embodiments, the current postural state includes activity information, performance information, fatigue information, and/or diagnosis information. The range of postural stability can be unique for the structure.

In some embodiments, the structure is a human and the load bearing structure is the human's lower extremities. The structure can be a human and the load bearing structure can be a cane, a crutch, a walker, a prosthetic leg, a walking aid, or any combination thereof. The structure can be a robotic device or a vehicle and the load bearing structure can be a leg and/or an axle coupled to one or more wheels.

In some embodiments, the pressure information is received from a plurality of sensors which are coupled to the load bearing structure. A message can be transmitted to the structure. The message can relate to the next postural state. In some embodiments, a message is transmitted to a stability management module. The message can include supplemental sensory information to stimulate the structure to modify the next postural state from unstable to stable. In some embodiments, a message is transmitted to a stability management module. The message can include weight adjustment information to modify the next postural state from unstable to stable.

In some embodiments, a safety device is activated based on the current postural state and/or the next postural state. A message can be transmitted to a communication module using a network. The message can include the current postural state, the next postural state, and/or the range of postural stability.

The system can also include a handheld portable stability device. The handheld portable stability device can include the stability processing module. In some embodiments, the system further includes a stability management module configured to adjust a weight device to modify the next postural state from unstable to stable. In some embodiments, the system further includes a safety device configured to activate based on the current postural state and/or the next postural state. The sensor can be positioned in or disposed relative to a sock, a shoe, a sole insert, a cane, a crutch, a walker, a walking aid, a prosthetic leg, a robotic leg, a vehicle, and/or an axle connected to one or more wheels.

Shoes can be designed with pressure sensors (e.g., pressure sensors inside the shoes) that can be utilized to track how a person is doing and how well the person is controlling their balance throughout the day. A postural stability device can be portable and can be utilized on a daily basis while the person is conducting daily activities. A person can be notified regarding a pending unstable postural state, which can prevent falls and/or injuries to the person. A postural stability of a person over a period of time can be tracked and monitored, which can allow for the monitoring and/or correction of the person's daily activities. Tracking of a person's postural stability can allow for the assessment of medical and/or physical therapy. The determination of postural stability can be utilized in connection with safety devices to protect against injuries.

Other aspects and advantages of the invention can become apparent from the following drawings and description, all of which illustrate the principles of the invention, by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DETAILED DESCRIPTION OF THE INVENTION

A postural state of a person or subject can be utilized to notify the person and/or activate a safety device. The method and system for determining a subject's postural state can include a pressure sensor. Pressure information is received from the pressure sensor. The pressure sensor can be coupled to, for example, the sole of a person's shoe. The pressure information can be utilized to determine a current postural state of the person. A next postural state (e.g., a subsequent postural state) of the person can be determined using a Hidden Markov Model (HMM) calculation. The HMM calculation can utilize the current postural state of the person, a range of postural stability associated with the person, and/or probabilities of the transitions between the current postural state and the next postural state. The next postural state can be utilized to take corrective action to change the next postural state from unstable to stable (e.g., weight management device utilized to redistribute weight, stimulate the feet of the person), to activate a safety device (e.g., airbag, inflatable under garments), and/or to notify the person regarding the next postural state (e.g., "Warning—You May Fall!," "Sit Down Immediately!").

The illustrative embodiments as described herein can be utilized, for example, by physical therapists, doctors, athletes, astronauts, patients, and/or any person that needs to assess and/or correct postural stability. The illustrative embodiments as described herein can, for example, quantify the vestibular and other sensory feedback systems of the body which are used to maintain balance during quiescent standing, locomotion (e.g., running, walking), and/or other sensory-motor activities (e.g., dancing, kneeling). For example, a physical therapist can utilize the postural states to gauge the progress of a stroke patient as the patient relearns skills such as standing, walking, and/or running. As another example, the postural states could be utilized to help train athletes by quantifying their daily behavior (e.g., time spent running, time spent sitting) during training.

Figure 1:
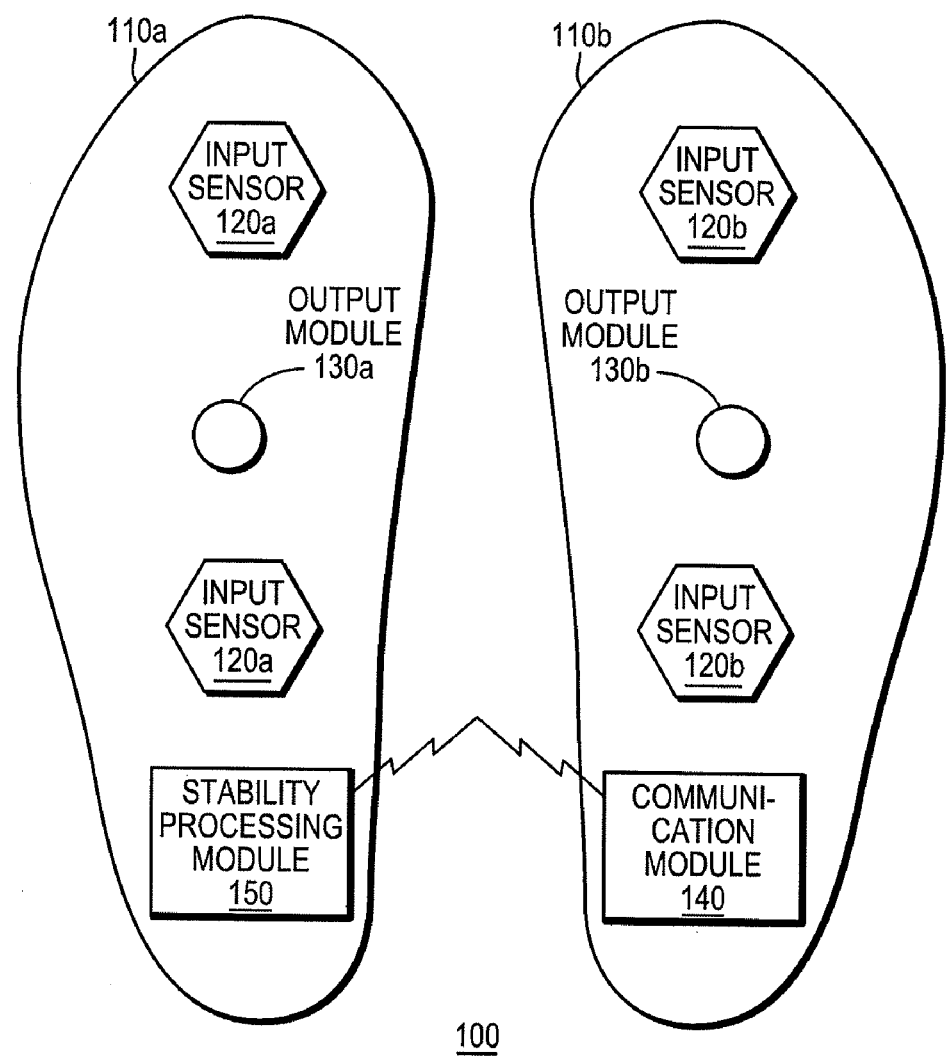
FIG. 1 is an exemplary diagram illustrating soles of a shoe which include a stability processing module, according to an illustrative embodiment of the invention.

FIG. 1 is an exemplary diagram 100 illustrating soles 110a and 110b (generally 110) of a shoe which can include a stability processing module 150, input sensors 120a and 120b (generally 120), output modules 130a and 130b (generally 130), and a communication module 140, according to an illustrative embodiment of the invention. The input sensors 120 measure sensor information (e.g., pressure information). The sensor information from the input sensors 120b can be transmitted to the communication module 140. The transmission from the input sensors 120b to the communication module 140 can be, for example, via a wire embedded into the sole 110b. The communication module 140 can transmit the sensor information from the input sensors 120b to the stability processing module 150. The transmission from the communication module 140 to the stability processing module 150 can be, for example, via a personal area network (PAN). The sensor information from the input sensors 120a can be transmitted to the stability processing module 150. The transmission from the input sensors 120a to the stability processing module 150 can be, for example, via a wire embedded into the sole 110a.

The stability processing module 150 determines the current postural state of the person associated with the soles 110 based on the sensor information. The stability processing module 150 can determine the next postural state of the person (e.g., a subsequent postural state of a person) based on a range of postural stability, the current postural state, and/or a probability of the next postural state.

If the next postural state is determined to be unstable (e.g., falling down, loss of equilibrium), then the stability processing module 150 can transmit a message to the output modules 130. The message transmitted to the output modules 130 can include instructions to modify the next postural state from unstable to stable. The output modules 130 can be, for example, vibration modules which vibrate to notify the person of the pending unstable state and/or to increase blood flow to the person's feet. The increased blood flow to the person's feet can, for example, provide the muscular strength and/or flexibility for the person to adjust his/her postural state.

For example, the input sensors 120 are pressure sensors 120 which sense the pressure of a person's foot in each of the soles 110. The pressure information sensed by the pressure sensors 120 in each of the soles 110 can be transmitted to the stability processing module 150. The pressure sensors 120a in the sole 110a with the stability processing module 150 can transmit the pressure information via a wire embedded into the sole 110a. The pressure sensors 120b in the sole 110a without the stability processing module 150 can transmit the pressure information via a wire embedded into the sole 110b to the communication module 140. The communication module 140 can transmit the pressure information wirelessly to the stability processing module 150.

The stability processing module 150 can determine the current postural state by calculating the center of force of the person utilizing the pressure information. The determination of the current postural state can utilize the HMM calculation. The HMM calculation can utilizes a set of probabilities for each postural state to determine the next postural state. If the next postural state is stable, then the stability processing module 150 can continue to monitor the person. If the next postural state is unstable, then the stability processing module 150 can activate the output modules 130 to vibrate which notifies the person that they may fall and should take corrective action immediately.

In some embodiments, the soles 110 are inserts for shoes. The soles 110 can be, for example, integrated into shoes. A stable equilibrium in a person can be, for example, described as a well-controlled posture while an unstable equilibrium can be a poorly controlled posture.

In some embodiments, the input sensors 120 are pressure sensors that measure pressure information. The input sensor 120 can be, for example, a motion sensor, a temperature sensor, a heat sensor, a dielectric sensor, an electrical sensor, a magnetic sensor, a flow sensor, a humidity sensor, a chemical sensor, a light sensor, a sound sensor, and/or any other type of sensor.

In some embodiments, the transmission of the sensor information from the communication module 140 to the stability processing module 150 is through a network. The network can be, for example, a network (e.g., wired, wireless).

In some embodiments, the output modules 130 are electrical output modules which output electrical pulses and/or mechanical output modules which output mechanical pulses and/or stimuli. The electrical pulses and/or the mechanical pulses can, for example, notify the person of the next postural state and/or can stimulate the person to modify the next postural state from unstable to stable. The stimulation can occur in real-time after the stability processing module 150 determines that the next postural state is unstable, which can prevent the person from falling while also improve circulation and/or muscle tone.

In some embodiments, the stability processing module 150 transmits the next postural state, the current postural state, the sensor information, and/or the range of postural stability to a postural analysis module (not shown). The postural analysis module can be, for example, a handheld portable device for use by the person wearing the sensor device, a handheld portable device for use by a person monitoring the person wearing the sensor device, part of a computing device (e.g., computer at doctor's office, computer at the person's home) used to automatically monitor the person wearing the sensor device, or any combination thereof. The transmission to the postural analysis module can be, for example, through a network (e.g., public switched telephone network (PSTN), a local area network (LAN), a radio area network (RAN), a personal area network (PAN), the internet). The postural analysis module can, for example, utilize the transmitted information to monitor, track, and/or notify the person regarding their postural states. The postural analysis module can, for example, store the transmitted information for historical analysis by the person being monitored and/or a third party monitoring the person (e.g., doctor, physical therapist).

In some embodiments, the stability processing module 150 transmits the current postural state and/or the sensor information to the postural analysis module. The postural analysis module can, for example, store the current postural state and/or the sensor information. The postural analysis module can, for example, determine a statistic (e.g., percentage of time running, percentage of time sitting), a score (e.g., number of falls per day, average number of falls per month), a simulation (e.g., with increased physical therapy will the number of falls decrease, with increased training can the athlete distribute his/her mass better), and/or any other type of metric based on the stored postural state and/or the stored sensor information. The postural analysis module can, for example, display the statistic, the score, and/or the simulation for use by the person being monitoring and/or the third party. The postural analysis module can, for example, store the statistic, the score, and/or the simulation.

In some embodiments, the postural state is stable or unstable. The postural state can, for example, include activity information (e.g., walking, running, sitting), performance information (e.g., time spent walking, time spent running), fatigue information (e.g., time spent close to outer range of postural stability, time spent close to center of postural stability), and/or diagnosis information (e.g., limp, lameness, neural condition, muscular condition, vision-related condition).

In some embodiments, the determination of a next postural state, current postural state, and/or past postural states utilizes a posterior decoding algorithm, a Bayesian segmentation, a graphical model, a choice-point method, and/or any other type of algorithm that classifies time periods into static and/or dynamic periods. A dynamic Bayesian network can be, for example, utilized to determine the next and/or past postural states based on the current postural state, the range of postural stability, and/or the probabilities of the next postural state.

In some embodiments, the determination of the next, current, and/or past postural states utilizes a forward algorithm, a Viterbi algorithm, a forwards-backwards algorithm, Baum-Welch algorithm, and/or any other type of algorithm that classifies time periods into static and/or dynamic periods. The forwards-backwards algorithm can be, for example, utilized to determine the probability of the next state (e.g., dynamic, equilibrium). The Viterbi algorithm can be, for example, utilized to determine the probability of the next state. The Baum-Welch algorithm can be, for example, utilized to determine the range of postural stability and/or the probabilities of transitioning between states.

In some embodiments, the HMM calculation determines the next state, the current state, and/or one or more past states (e.g., five, ten). The HMM calculation can be, for example, utilized to determine the probabilities of the sequence of the past states, the current state, and/or the next state. The sequence of the past states can be, for example, utilized to calculate the probability of the next state. The sequence of the past states can be, for example, utilized to determine the score, the statistic, and/or the simulation.

Although FIG. 1 illustrates soles 110 with two input sensors 120 each, the soles 110 can have a plurality of input sensors (e.g., four, ten, twenty, etc.). In some embodiments, only one of the soles 110 has input sensors 120. In some embodiments, there is only one input sensor 120 utilized for sensor information (i.e., there is only one input sensor 120 between the two soles 110).

In some embodiments, the range of postural stability is determined for the person utilizing the soles 110. The range of postural stability can be, for example, unique for the person since the range of postural stability can be affected by age, activity level, postural stance, weight, medical history, and/or any other factor that can affect a person's posture.

In some embodiments, the range of postural stability is determined based on sensor information which is stored by the stability processing module 150. The range of postural stability can be determined, for example, by processing the stable postural states to determine the range of stable postural states. The determination of the range of the postural stability can occur, for example, in real-time while the user is wearing the shoes with the soles 110.

In some embodiments, the range of postural stability is based on a person's center of gravity. A person's center of gravity can vary, for example, in a range because a human can be modeled as an inverted pendulum in which an upright stance is an unstable equilibrium. Since small natural center of mass deviations (e.g., breathing, limb movements, head movement) can disrupt the equilibrium, then the pendulum (i.e., which can represent the person) can top over without appropriate sensory-motor control system. Generally, standing posture utilizes subconscious sensory feedback mechanisms (e.g., vision, tactile sensations, vestibular organs) to maintain upright stance (i.e., a stable postural state). An advantage of determining the postural stability of a person is that the person can have a real-time readout of their capacity to balance at any given point in time.

In some embodiments, the range of postural stability is pre-determined for the person based on preset parameters. For example, there can be preset parameters based on a person's age, weight, height, activity level, and/or any other type of parameter associated with posture.

In some embodiments, the range of postural stability is a global optimum. The global optimum indicates, for example, that there is a single optimal point for upright posture. If a person is not at the optimum, then the person's body always directs the person towards the optimum.

In other embodiments, the range of postural stability is a safe zone. The safe zone can be, for example, a zone of upright posture. Inside this zone, a person is stable in regards to postural stability and a person moves around this zone at random. Every person can, for example, have a safe zone. The safe zone for every person can be, for example, unique from other safe zones.

In some embodiments, the range of postural stability is a punctuated equilibrium. The punctuated equilibrium can be, for example, a safe zone with a constant turnover of equilibria. This transient equilibria form, persist, and dissipates following control failure (e.g., not in equilibrium, including falling down). Following a control failure, a new equilibria forms and control is restored.

Although FIG. 1 illustrates a person wearing a shoe, the input sensors 120 can be coupled to a load bearing structure associated with a structure such that the postural states are determined for the structure. The structure can be, for example, a vehicle and/or any other type of structure associated with a load bearing structure. The load bearing structure can be, for example, a leg, an axle couple to one or more wheels, and/or any other type of structure that is load bearing. In some embodiments, the structure is a car and the load bearing structures are the axles coupled to the wheels, where the input sensors 120 are coupled to the axles.

In some embodiments, the input sensors 120 are coupled to a bed to receive input information associated with the person on the bed. The input sensors 120 can be, for example, coupled to a seat of a chair to receive input information associated with the person sitting in the chair. For example, the input sensors 120 can be coupled to the seat in a car. When the stability processing module 150 determines that the current postural state and/or the next postural state is the person being ejected from the seat (e.g., in an accident), then the stability processing module 150 can activate a safety device (e.g., air bag, anti-lock brakes).

In some embodiments, the output module 130 is coupled to the bed and/or chair. The output module 130 can be, for example, a mechanical stimulator which can activate when the person has been sitting and/or lying for a set period of time (e.g., one minute, twenty minutes). For example, the stability processing module 150 is set to activate the mechanical stimulator for one minute every sixty minutes of sitting. When the stability processing module 150 determines that the person has been sitting for sixty minutes (e.g., continuous sitting, accumulative sitting), then the mechanical stimulator is activated for one minute. A person's muscles can be automatically stimulated based on inactivity to prevent muscle decay due to the inactivity.

Figure 2:
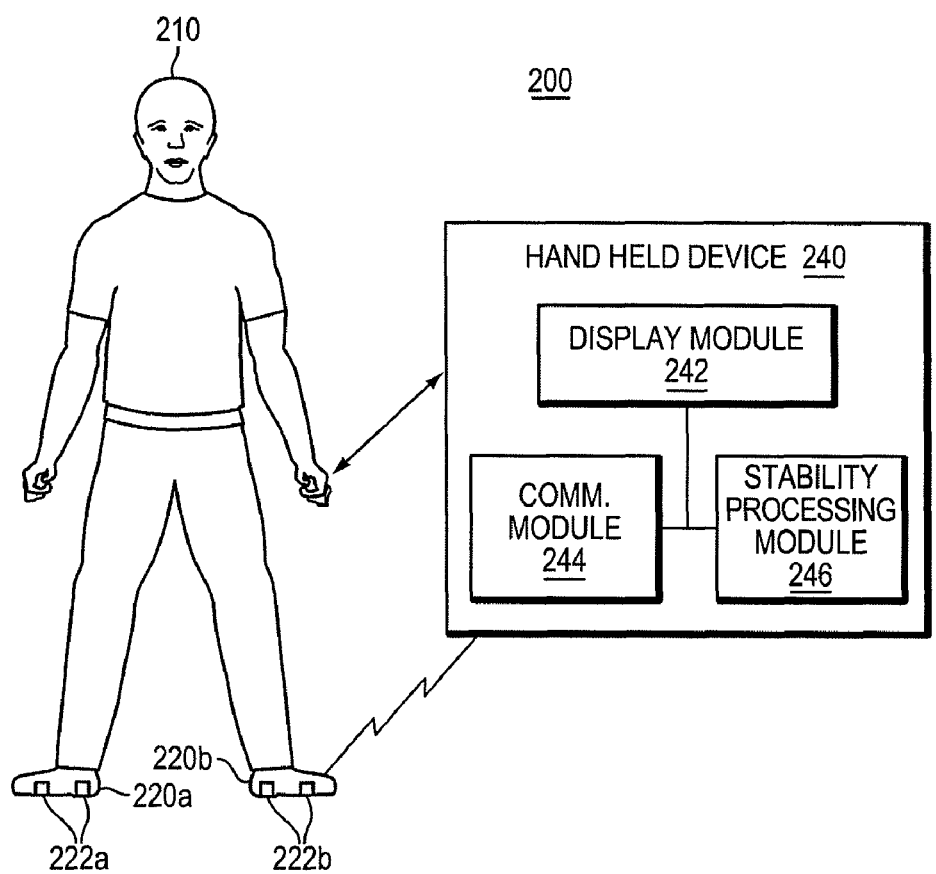
FIG. 2 is an exemplary diagram illustrating a human with a handheld stability device, according to an illustrative embodiment of the invention.

FIG. 2 is an exemplary diagram 200 illustrating a person 210 with a handheld stability device 240, shoes 220a and 220b (generally 220), and input sensors 222a and 222b (generally 222), according to an illustrative embodiment of the invention. In this embodiment, the person 210 is wearing shoes 220. Each of the shoes 220 can have input sensors 222. The input sensors 222 can receive sensor information associated with the person. The input sensors 222 can transmit the sensor information to a communication module 244 in the handheld device 240. The communication module 244 can transmit the sensor information to the stability processing module 246. The stability processing module 246 can determine the current postural state and the next postural state. The current postural state and the next postural state can be displayed on the display module 242.

In some embodiments, a message is transmitted from the stability processing module 246 to the display module 242. The message can be displayed on the display module 242. The message can include information informing the person of a stable equilibrium (e.g., "Great Stance!," "Stand Straight!"), instructional information informing the person to take action to not fall (e.g., "Sit Down!," "Warning—You may Fall!"), reporting information (e.g., "You ran two hours today," "You have been sitting too long today."), and/or any other type of information collected and/or utilized by the handheld device. The reporting information can include information generated and/or determined by the stability processing module 246 which can include the score, the statistic, and/or the simulation.

In some embodiments, the communication module 244 receives sensor information through a wireless network (e.g., PAN, RAN) from the input sensors 222.

In some embodiments, the display module 242 is a liquid crystal display (LCD) device which displays information (e.g., corrective information, current posture information). The display module 242 can be, for example, a light emitting diode (LED) and/or any other type of display which notifies the person 210 of the postural states. In some embodiments, the legs of the person 210 are the load bearing structures and the person 210 is the structure.

In some embodiments, the handheld device 240 and the input sensors 222 are utilized to determine the postural stability of an astronaut after a spaceflight. The changes in gravitational field strength during a spaceflight can, for example, disrupt the postural stability of an astronaut. The handheld device 240 can allow for the tracking of the astronaut's postural stability on a long-term basis without interfering with the astronaut's daily activities. In some embodiments, the handheld device 240 and the input sensors 222 are utilized to monitor the postural state of an astronaut during spaceflight and/or environments of altered gravity (e.g., on the moon, on mars).

In some embodiments, the handheld device 240 is a portable handheld device 240. The portable handheld device 240 can be utilized during a person's daily activities and may not interfere with the collection of sensor information and/or postural states during normal activity.

Although FIG. 2 illustrates the handheld device 240 associated with the person 210 that is associated with the sensor information, the handheld device 240 can be utilized by a third party (e.g., physical therapist, doctor) to track the postural states of the person (e.g., a patient, an athlete). The third parties can track the progress of the patient as the patient relearns skills such as standing, walking, and/or running via the handheld device 240.

In some embodiments, the input sensors 222 communicate via a wireless network (e.g., PAN, RAN) to a remote computing device (not shown) which is utilized by third parties (e.g., caregiver, doctor) to monitor the person's postural stability. The remote computing device can, for example, store the sensor information. The remote computing device can, for example, determine the statistic, the score, the simulation, and/or any other type of information based on the sensor information.

In some embodiments, the input sensors 222 are coupled to any load bearing structure (e.g., person's lower extremities, socks) associated with the structure (in this example, the person).

Although FIG. 2 illustrates a person 210 with shoes 220, the person 210 can be in a spacesuit and the shoes 220 can be the boots of the spacesuit. The input sensors 222 can be coupled to the boots and/or the other lower extremities of the spacesuit. The handheld device 240 can be integrated into the other devices and/or modules of the spacesuit.

Figure 3:
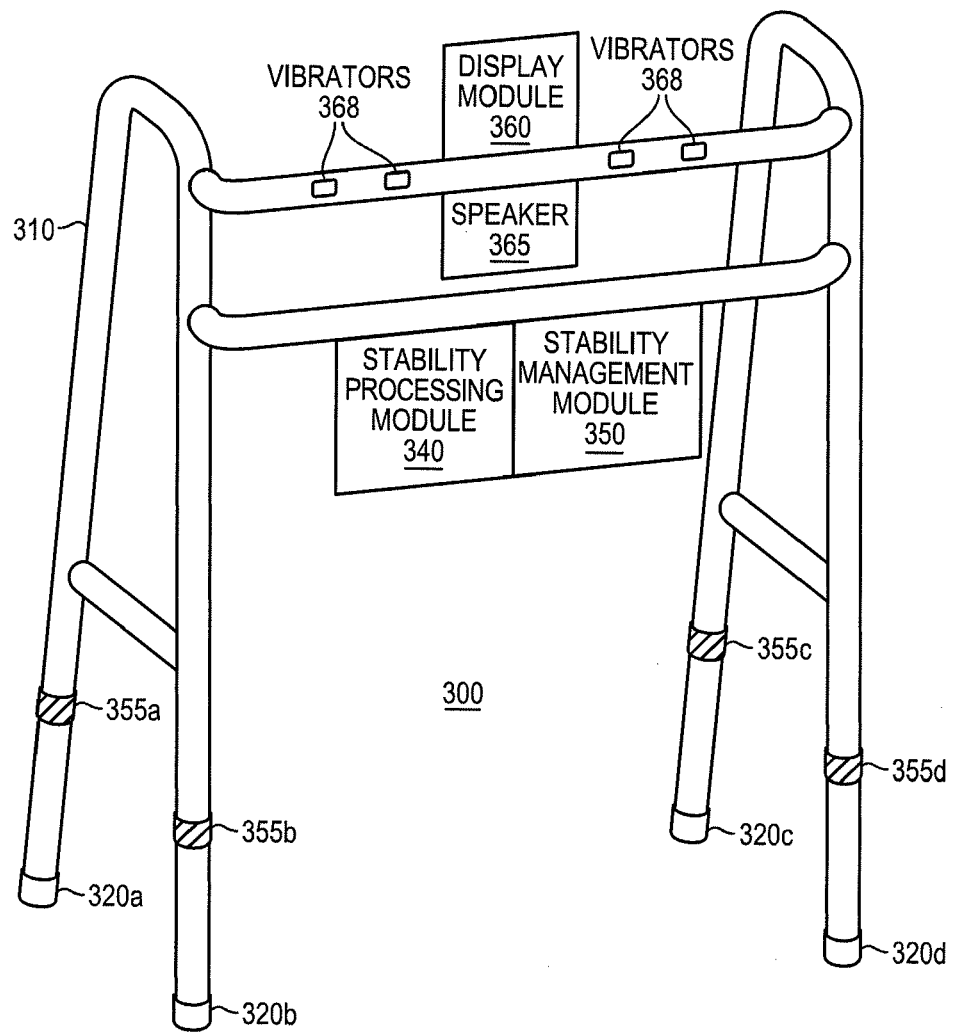
FIG. 3 is an exemplary diagram illustrating a walker with a stability module, according to an illustrative embodiment of the invention.

FIG. 3 is an exemplary diagram 300 illustrating a walker 310 with a stability processing module 340, a stability management module 350, a display module 360, a speaker 365, vibrators 368, input sensors 320a, 320b, 320c, and 320c (generally 320), and weight devices 355a, 355b, 355c, and 355d (generally 355), according to an illustrative embodiment of the invention. The walker can include input sensors 320 which are coupled to each leg of the walker 310. The input sensors 320 can receive input information and can transmit the input information to the stability processing module 340. The stability processing module 340 can determine the current postural state.

The stability processing module 340 can determine the next postural state based on the current postural state, the range of postural stability, and/or the probabilities of the next postural state. If the next postural state is unstable, then the stability processing module 340 can send a message to the stability management module 350. Based on this message, the stability management module 350 can transmit instructions for the speaker 365 to announce a warning (e.g., "Sit Down!," "Unstable State!"), for the display module 360 to display a warning, for the vibrators 368 to vibrate, and/or for the weight devices 355 to adjust to stabilize the walker 310 and/or the person. The weight devices 355 can be coupled to each of the legs of the walker 310.

In some embodiments, the current postural state can be transmitted to the display module 360. The display module 360 can display the current postural state. For example, if the current postural state is stable, then the display can be "Stable Posture." If the current postural state is unstable, then the display can be "Unstable—Sit Down Immediately!"

In some embodiments, the stability processing module 240 and/or the stability management module 350 are utilized to auto balance the walker 310. The auto balance can utilize weight devices 355 to balance the walker 310.

Although FIG. 3 illustrates a weight device (e.g., 355a) coupled to each of the legs of the walker 310, the walker 310 can have one weight device (e.g., 355) that could be centrally mounted on the walker 310. The centrally mounted weight device (e.g., 355a) can be utilized to modify the postural state of the walker 310 and/or person from unstable to stable.

Figure 4:
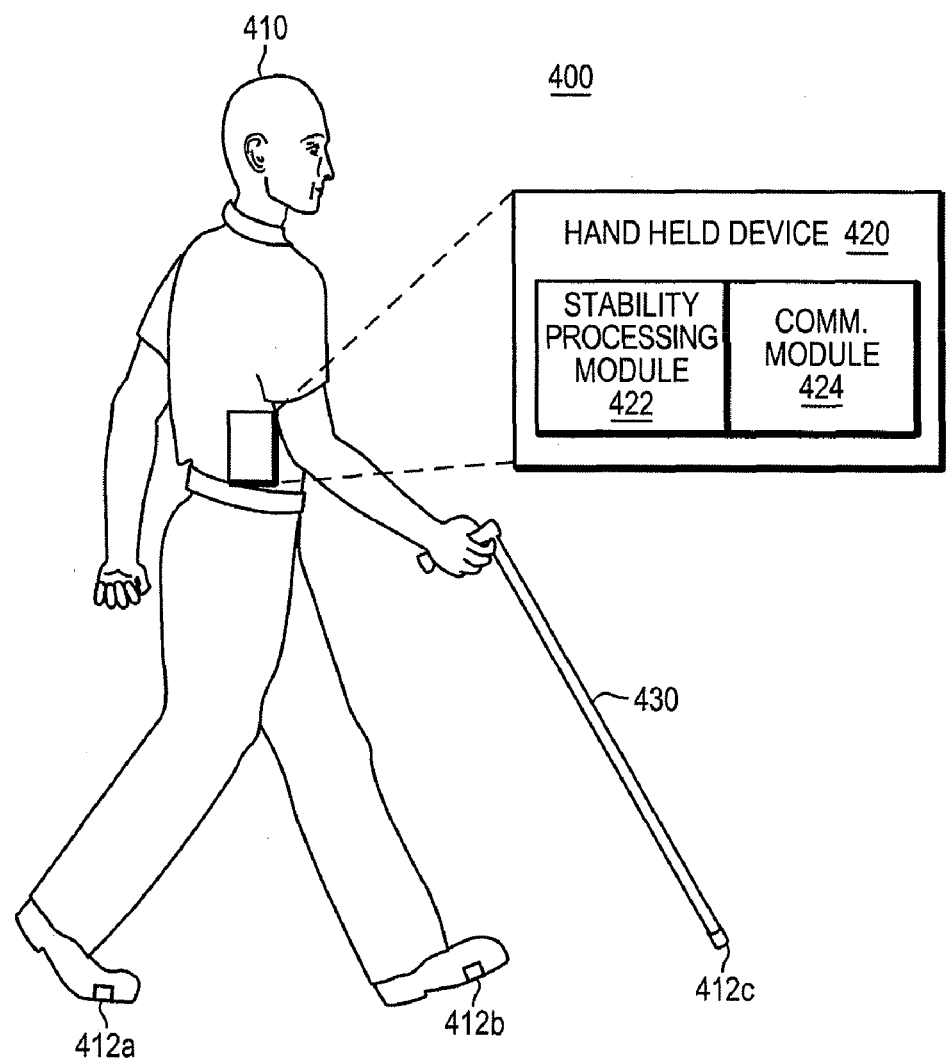
FIG. 4 is an exemplary diagram illustrating a person with a cane and a handheld stability device, according to an illustrative embodiment of the invention.

FIG. 4 is an exemplary diagram 400 illustrating a person 410 with a cane 430, a handheld stability device 420, and input sensors 412a, 412b, and 412c (generally 412), according to an illustrative embodiment of the invention. The person 410 can utilize cane 430 and the person's feet as load bearing structures. The input sensors 412 can be coupled to the person's shoes and the cane 430, respectively. The input sensors 412 can transmit input information to the communications module 424 via a network (e.g., PAN, RAN). The communications module 424 can transmit the input information to the stability processing module 422. The stability processing module 422 can determine the current postural state and the next postural state of the person.

Although FIG. 4 illustrates the person 410 utilizing the cane 430, the person 410 could be utilizing a crutch, a prosthetic leg, and/or any other walking aid. The input sensors 412 can be coupled to any of these load bearing structures.

Figure 5:
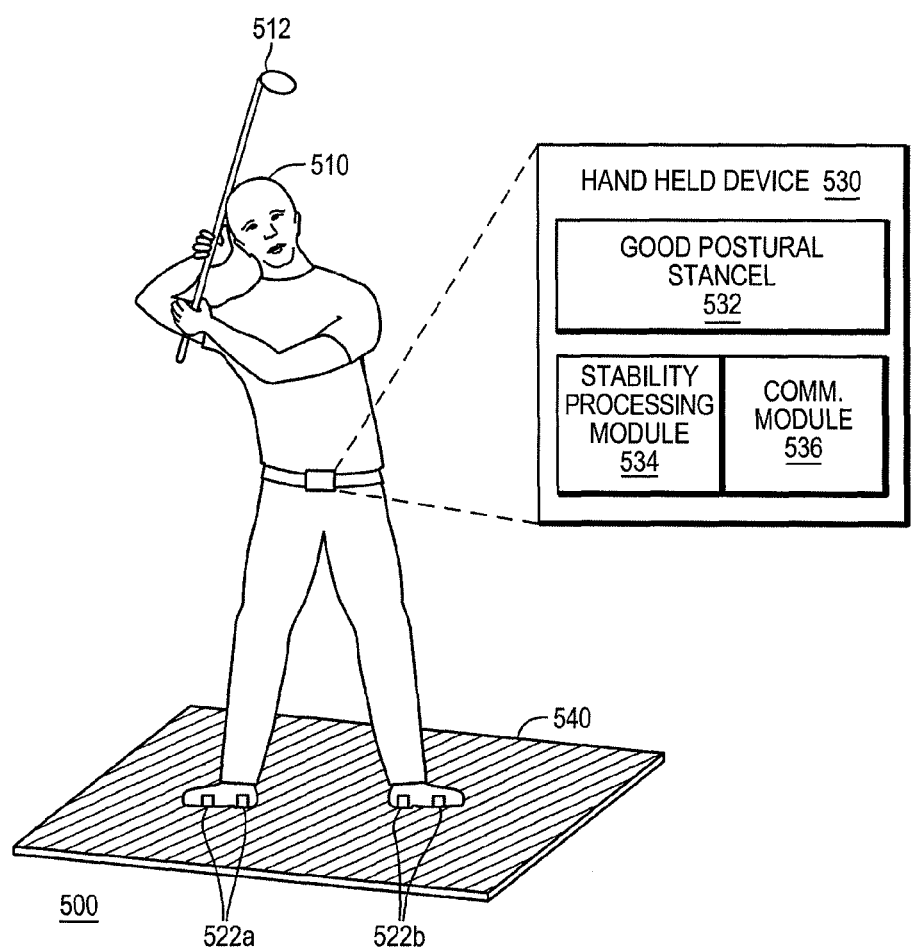
FIG. 5 is an exemplary diagram illustrating a person playing golf with a handheld stability device, according to an illustrative embodiment of the invention.

FIG. 5 is an exemplary diagram 500 illustrating a person 510 playing golf utilizing a golf club 512, a handheld stability device 530, a stability processing module 534, a communication module 536, and input sensors 522a and 522b (generally 522), according to an illustrative embodiment of the invention. The person's shoes 510 can include input sensors 522 which receive sensor information. The sensor information can be transmitted to the communications module 536 via a network (e.g., PAN, RAN). The communications module 536 can transmit the sensor information to the stability processing module 534.

The stability processing module 534 can determine the current postural state based on the sensor information. The current postural state can be transmitted to the display module 532 which displays the postural state (e.g., "Good Postural Stance!"). The stability processing module 534 can process a simulation to determine if any changes can be made to the person's posture to The stability processing module 534 can determine the next postural state based on the current postural state, the range of postural stability, and/or the probability of the next postural state. The probability of the next postural state can be, for example, customized according to sporting activity. For example, since football includes external forces acting on the person (i.e., one or more third parties tackling the person), then the probabilities of the next postural state can take those external forces into account (e.g., the probability that the next postural state changes from running to tackled may be 0.9 for a football player while the probability is only 0.1 for a track runner).

Although FIG. 5 illustrates the handheld postural device 530 utilized to analyze the person's golf game, the handheld postural device 530 can be utilized for other activities (e.g., sports). For example, the handheld postural device 530 can be utilized for track and field, American football, baseball, cricket, soccer, basketball, hockey, bowling, gymnastics, skiing, figure skating, dance and/or any other type of sporting activity.

Figure 6:
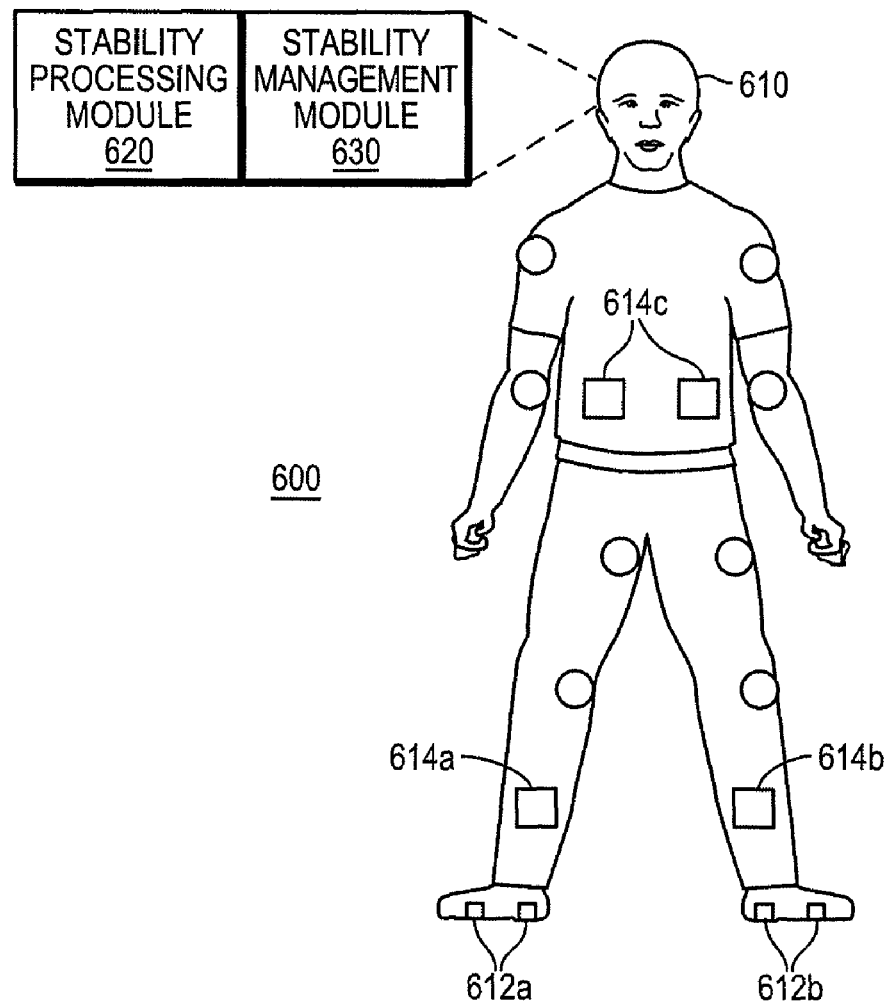
FIG. 6 is an exemplary diagram illustrating a robot with a stability module, according to an illustrative embodiment of the invention.

FIG. 6 is an exemplary diagram 600 illustrating a robot 610 with a stability processing module 620, a stability management module 630, input sensors 612a and 612b (generally 612), and weight devices 614a, 614b, and 614c (generally 614), according to an illustrative embodiment of the invention. The robot 610 can have input sensors 612. The input sensors 612 can be coupled to the load bearing structures of the robot 610 (i.e., the legs of the robot 610). The input sensors 612 can receive input information (e.g., pressure information from each leg of the robot 610). The input sensors 612 can transmit the input information to the stability processing module 620. The stability processing module 620 can determine the current postural state of the robot 610 based on the input information. If the current postural state is unstable, then the stability processing module 620 can transmit a message to the stability management module 630. The message can include information regarding the instability (e.g., all of the weight is on the left leg, weight is not distributed evenly). Based on the message, the stability management module 630 can transmit a message to the weight devices 614 to adjust the weight balance of the robot 610. These adjustments by the stability management module 630 can be used to modify the postural state from unstable to stable.

The stability processing module 620 can determine the next postural state based on the current postural state, the range of postural stability, and/or the probability of the next postural state.

In some embodiments, the range of postural stability is predetermined for the model of the robot 610. For example, Model R2 robots can have a set range of postural stability based on the distribution of their components. In some embodiments, the range of postural stability is determined in real-time based on the configuration of the robot 610. For example, the robot 610 can determine which modules (e.g., extra battery, welder attachment, voice processor) it contains and determines the range of postural stability based on its included modules.

Figure 7:
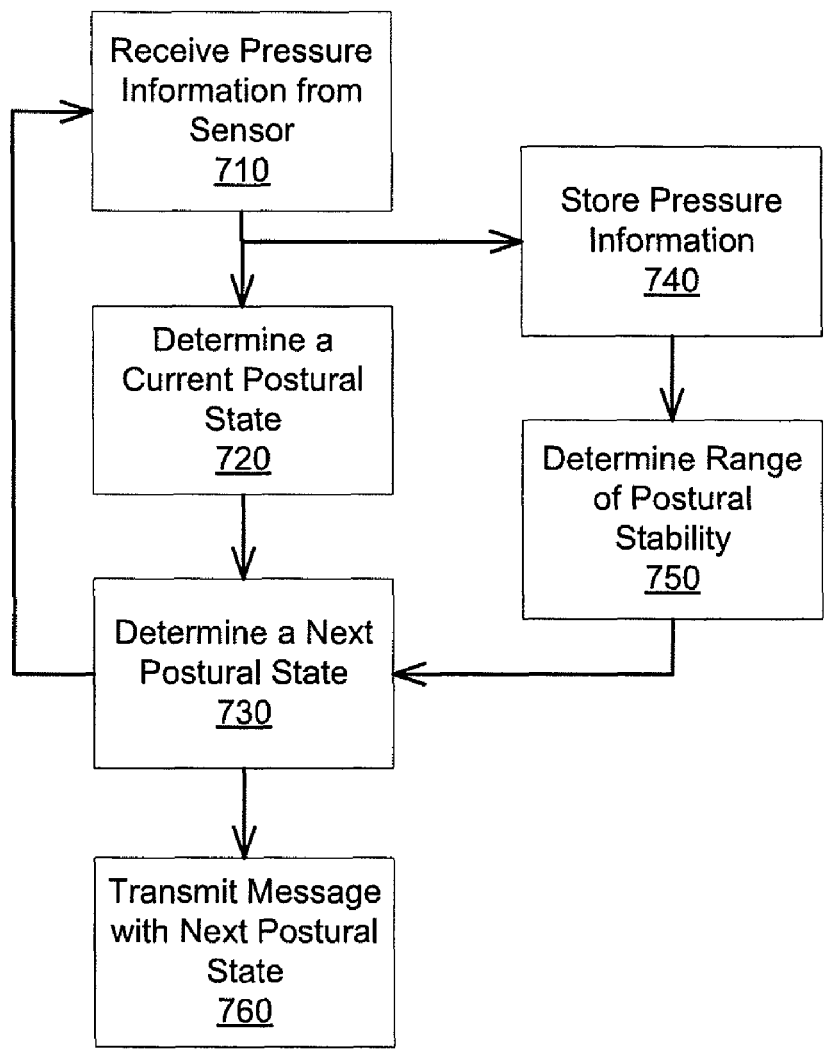
FIG. 7 is an exemplary flowchart illustrating the determination of postural states, according to an illustrative embodiment of the invention.

FIG. 7 is an exemplary flowchart 700 illustrating the determination of postural states utilizing the exemplary diagram 200 of FIG. 2, according to an illustrative embodiment of the invention. The communication module 244 receives (710) the pressure information (e.g., pressure data points) from the sensors 222. The pressure information can be acquired over a period of time. The pressure information can be communicated to the stability processing module 246. The stability processing module 246 can determine (720) the current postural state of the person 210 based on the pressure information and store (740) the pressure information. Based on the stored pressure information, the stability processing module 246 determines (750) the range of postural stability.

The stability processing module 246 can determine (730) the next postural state of the person 210 (e.g., a subsequent postural state of the person) based on the current postural state, the range of postural stability, and/or the probability of the next postural state. The stability processing module 246 can transmit (760) a message which includes the next postural state to the display module 242 for display to the person 210. After the stability processing module 246 determines (730) the next postural state, the processing can receive (710) the next set of pressure information from the sensors 222.

Figure 8:
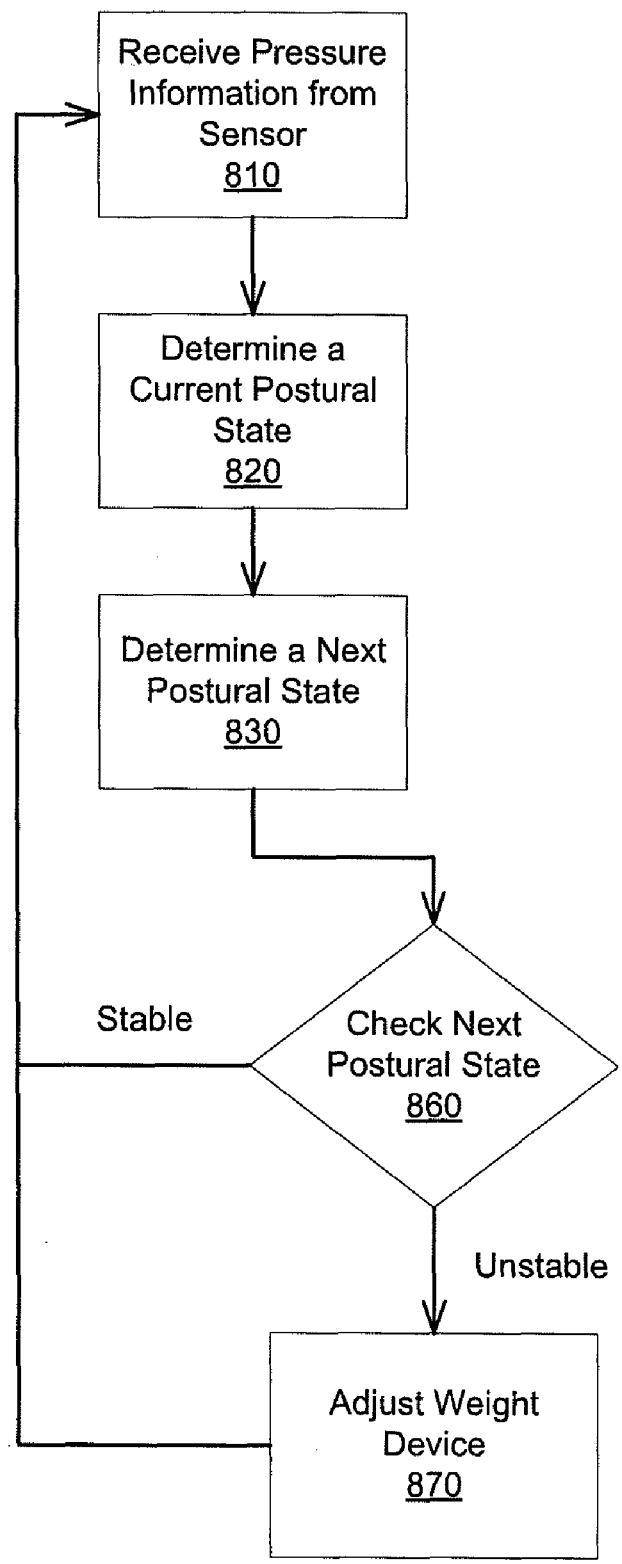
FIG. 8 is an exemplary flowchart illustrating the checking of postural states, according to an illustrative embodiment of the invention.

FIG. 8 is an exemplary flowchart 800 illustrating the checking of postural states utilizing the exemplary diagram 600 of FIG. 6, according to an illustrative embodiment of the invention. The stability processing module 620 can receive (810) the pressure information from the sensors 612. The stability processing module 620 can determine (820) the current postural state of the robot 610 based on the pressure information.

The stability processing module 620 can determine (830) the next postural state of the robot 610 based on the current postural state, the range of postural stability, and/or the probability of the next postural state. The stability processing module 620 can check (860) the next postural state. If the next postural state is stable, then the processing can continue by receiving (810) the next set of pressure information from the sensors 612. If the next postural state is unstable, then the stability processing module 620 can utilize the stability management module to adjust (870) the weight devices 614. The adjustment (870) of the weight devices 614 can modify the next postural state from unstable to stable.

Although FIG. 8 illustrates the adjustment (870) of weight devices 612 in unstable states, the weight devices can also be adjusted (870) to modify the next postural state from one state to another state (e.g., standing to sitting, dynamic to equilibrium, running to walking).

In some embodiments, the probability of transitioning between postural states is determined. The probabilities can be, for example, determined based on the stored sensor information and/or the range of postural stability.

Figure 9:
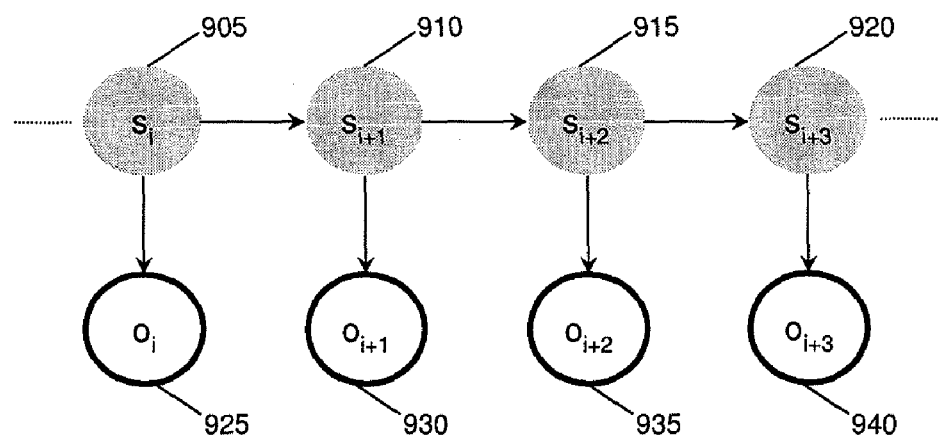
FIG. 9 shows a state graph, according to an illustrative embodiment of the invention.

For example, the HMM calculation utilizes various states (e.g., current state, one or more past states) and the probabilities of the hidden states (e.g., current state, one or more past states) to determine the next postural state. FIG. 9 depicts a state graph, according to an illustrative embodiment of the invention. By way of example, if the state graph in FIG. 9 is utilized with tables 1 and 2, then the probability of the next postural state can be determined. As shown in FIG. 9 for each state 905-920 there can be corresponding observations 925-940. $S_i$ (905), $S_{i+1}$ (910), $S_{i+2}$ (915), and $S_{i+3}$ (920) represent the states and $O_i$ (925), $O_{i+1}$ (930), $O_{i+2}$ (935), and $O_{i+3}$ (940) represent the possible observations.

TABLE 1

Emission Probability

|  |  | $S_i$ | |
|---|---|---|---|
|  |  | Equilibrium | Dynamic |
| $O_i$ | Fast Velocity | 0.2 | 0.7 |
|  | Slow Velocity | 0.8 | 0.3 |

TABLE 2

Transition Probability $S_{i+1}$

|       |             | Equilibrium | Dynamic |
|-------|-------------|-------------|---------|
| $S_i$ | Equilibrium | 0.98        | 0.02    |
|       | Dynamic     | 0.32        | 0.68    |

In some embodiments, the observation $O_i$ (925) is utilized with the past states (e.g., $S_{i-1}$, $S_{i-2}$, $S_{i-3}$) and the probabilities of the sequence of the past states to determine the probability of the current state $S_i$ (905). The probabilities of the observation $O_i$ (925) in the emission probability, table 1 (e.g., which can be used to determine an emission matrix), and the transition probability, table 2 (e.g., which can be used to determine a transition matrix), can be, for example, utilized together to determine the probability of the current state $S_i$ and/or the next state $S_{i+1}$. For example, if the past four states were equilibrium, then the probability that the current state will stay in equilibrium, the probability that the current state will change to dynamic, and the probability of the state associated with the observation is utilized to determine the current state and/or the next state. As another example, if the sequence of the past four states is equilibrium, dynamic, equilibrium, and equilibrium, then the probability of these transitions in relation to each other, the probability of the current state changing or staying the same (in this example, equilibrium), and the probability of the state associated with the observation is utilized to determine the current state and/or the next state. The context of the transitions and/or no transitions (e.g., the lack of transitioning) between the past states is utilized to determine the next state, thereby providing the calculation with a history.

In some embodiments, the dynamic state represents three possible outcomes: return to present equilibrium, transition to new equilibrium, or falling down. In some embodiments, the observations include sitting, standing, kneeling, lying down, falling, and/or any other postural position of a structure (e.g., person, robot). In some embodiments, the observations (e.g., $O_i$) include any type of observation of postural state (e.g., falling, standing, running, walking).

In some embodiments, velocity includes the center of mass velocity for the structure. The center of mass velocity can be, for example, measured by the input sensors (e.g., pressure sensors). The slow velocity and fast velocity can be, for example, relative (e.g., determined by comparing the measured center of mass velocity).

In some embodiments, the HMM calculation utilizes various states and the probabilities of the next hidden state to determine the next postural state. By way of example, if the state in FIG. 9 is utilized with tables 3 and 4, then the probability of the next postural state can be determined.

TABLE 3

| Emission Probability | | | | |
|---|---|---|---|---|
| | $S_i$ | | | |
| | Dynamic Standing | Equilibrium Standing | Walking | Running |
| $O_i$ Fast Gait and Fast Velocity | 0.15 | 0.01 | 0.04 | 0.60 |
| Fast Gait and Slow Velocity | 0.20 | 0.03 | 0.30 | 0.06 |
| Slow Gait and Fast Velocity | 0.40 | 0.01 | 0.06 | 0.32 |
| Slow Gait and Slow Velocity | 0.05 | 0.05 | 0.60 | 0.02 |
| Slow Gait and | 0.20 | 0.30 | 0.00 | 0.00 |

TABLE 3-continued

| Emission Probability | | | | |
|---|---|---|---|---|
| | $S_i$ | | | |
| | Dynamic Standing | Equilibrium Standing | Walking | Running |
| No Velocity No Gait and No Velocity | 0.00 | 0.60 | 0.00 | 0.00 |

TABLE 4

| Transition Probability | | | | |
|---|---|---|---|---|
| | $S_{i+1}$ | | | |
| | Dynamic Standing | Equilibrium Standing | Walking | Running |
| $S_i$ Dynamic Standing | 0.60 | 0.30 | 0.05 | 0.05 |
| Equilibrium Standing | 0.25 | 0.60 | 0.10 | 0.05 |
| Walking | 0.20 | 0.05 | 0.60 | 0.15 |
| Running | 0.12 | 0.10 | 0.18 | 0.60 |

In some embodiments, the stability processing module (e.g., 246 of FIG. 2) analyzes the range of postural stability to determine the current postural state and/or the next postural state. If the received pressure information is within set parameters of the range (e.g., 25% to 75%, 10% to 90%), then the stability processing module can determine that the next postural state is equilibrium (e.g., equilibrium running, equilibrium walking). If the received pressure information is not within the set parameters of the range, then the stability processing module can determine that the next postural state is dynamic (e.g., dynamic falling, dynamic walking).

In some embodiments, the probabilities of two or more possible next postural states are the same and/or substantially similar, so the next postural state may not be determined. The stability processing module (e.g., 246 of FIG. 2) can process the input information received from the input sensors, the range of postural stability, and/or the current postural state to determine the next postural state.

In some embodiments, the stability processing module (e.g., 246 of FIG. 2) processes the input information received from the input sensors, the range of postural stability, the current postural state, and/or the next postural state to determine if activity (e.g., alarm, email, notification) should be initiated based on the processing.

In some embodiments, the processing applies one or more rules to determine if a condition occurs. By way of example, a rule can include determining whether the person entered a dynamic state more than ten times in a thirty minute period. A rule can also include determining if, for example, the person has been in a dynamic state for 75% of the time over the past twenty four hours. The rules can be, for example, predetermined (e.g., set of rules based on age, set of rules based on a medical condition) and/or automatically generated (e.g., the person is usually in equilibrium 90% of the time in a two hour period so any percentage less than 90% in a two hour period sends an email to the person's caregiver). The automatically generated rules can be, for example, based on individual characteristics of the structure (e.g., specific percentage of state over time, number of times in dynamic state per hour), general characteristics of the structure (e.g., age range, medical condition), and/or any other metric associated with the structure. The activity initiated can be, for example, setting off the alarm, notifying the structure, notifying the third party (e.g., sending an email to the doctor, sending a text message to the caregiver), and/or any other type of notification and/or alarm. In some embodiments, an average velocity (e.g., of the person or other load bearing structure) can be measured during a window of time and the rule can be based on, for example, a number of velocity emission states out of a number of time period (e.g., whether there are more than 100 high-velocity emission states out of 150 time periods, etc.)

Figure 10:
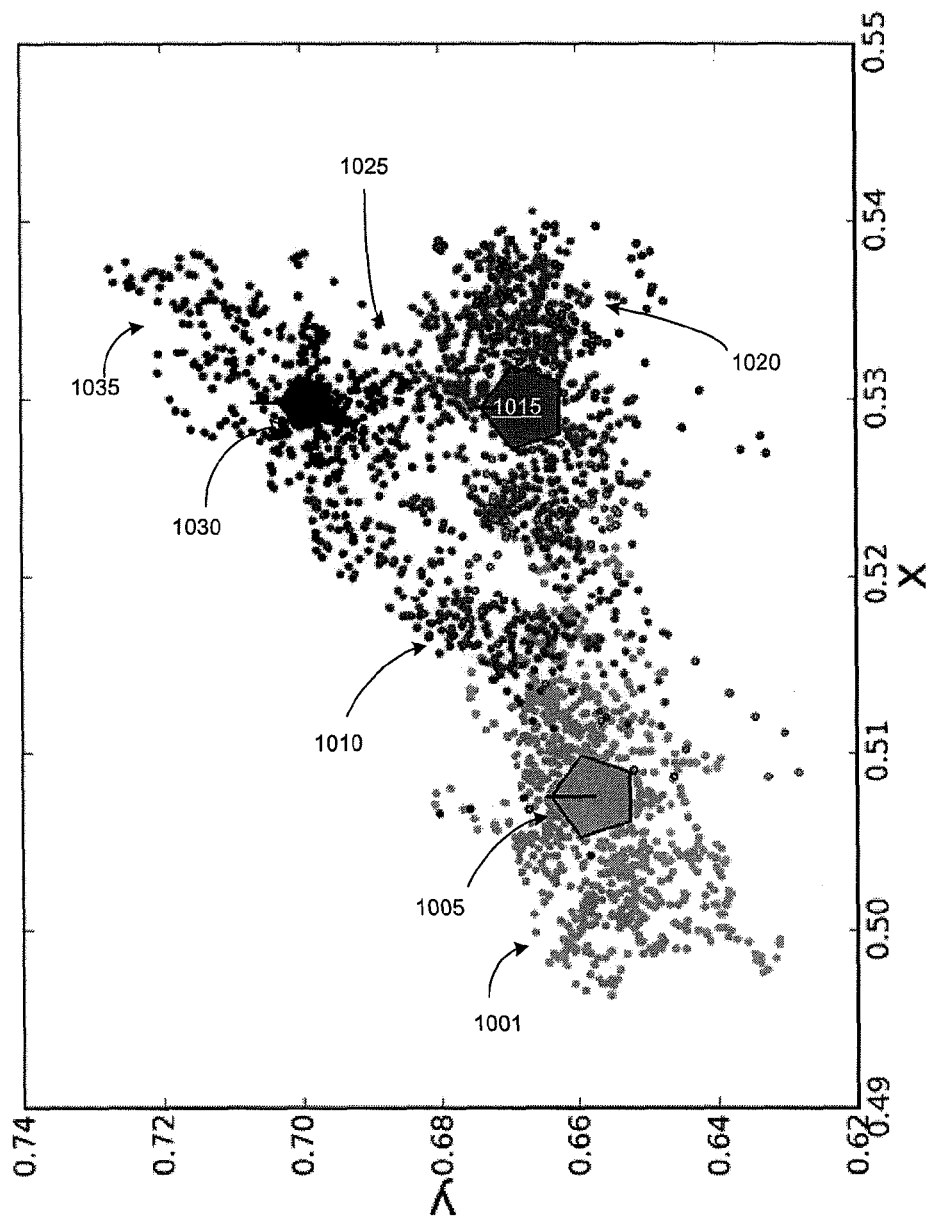
FIG. 10 is an exemplary chart illustrating equilibrium, according to an illustrative embodiment of the invention.

FIG. 10 illustrates an exemplary punctuated equilibrium during quiescent standing based on pressure points acquired from a sensor (e.g., sensor from the shoe, walker, prosthetic leg, walking aid, portion of a robotic device or other load bearing structure as described herein), according to an illustrative embodiment. In this example, the sensor was located on a shoe worn by a person/subject (i.e., person) that stood for two minutes on an EquiTest platform (available from Neuro-Com International of Clackamas, Oreg.). Pressure was sampled at the right toe, the right heel, the left toe, and the left heel, at a rate of one hundred Hz. The sensor data was classified by the HMM. Center-of-force from left foot (0.0) to right foot (1.0) is shown on the x-axis. Center-of-force in the anterior (1.0) to posterior (0.0) direction is plotted on the y-axis, normalized by foot length. The subject's center-of-force was initially dynamic 1001 (e.g., as indicated by light shading), but settled into an initial equilibrium 1005 (e.g., as indicated by lighter shading). A dynamic escape trajectory 1010 (e.g., as indicated by lighter shading with light border) led to settling in a second equilibrium 1015 (e.g., as indicated by medium shading). A dynamic reversion trajectory 1020 (e.g., as indicated by medium shading with dark border) did not disturb the equilibrium, but a subsequent escape trajectory 1025 (e.g., as indicated by medium shading with light border) led the subject to settle into a final equilibrium 1030 (e.g., as indicated by dark shading). Towards the end of the two minutes, the subject entered a dynamic trajectory 1035 (e.g., as indicated by dark shading with light border). In FIG. 10, pentagons were used to mark the center-of-force of each equilibrium. The pentagon size can correspond to dwell time. The length of the embedded line can be the average distance of each point in the equilibrium from the equilibrium center-of-mass, a measure of the compactness of the equilibrium. In some embodiments, the center-of-force information is utilized for the range of postural stability. For example, the range of pressures collected from the subject while the subject is standing is used to create the range of postural stability. The range of postural stability can be utilized to determine the next postural state.

Figure 11:
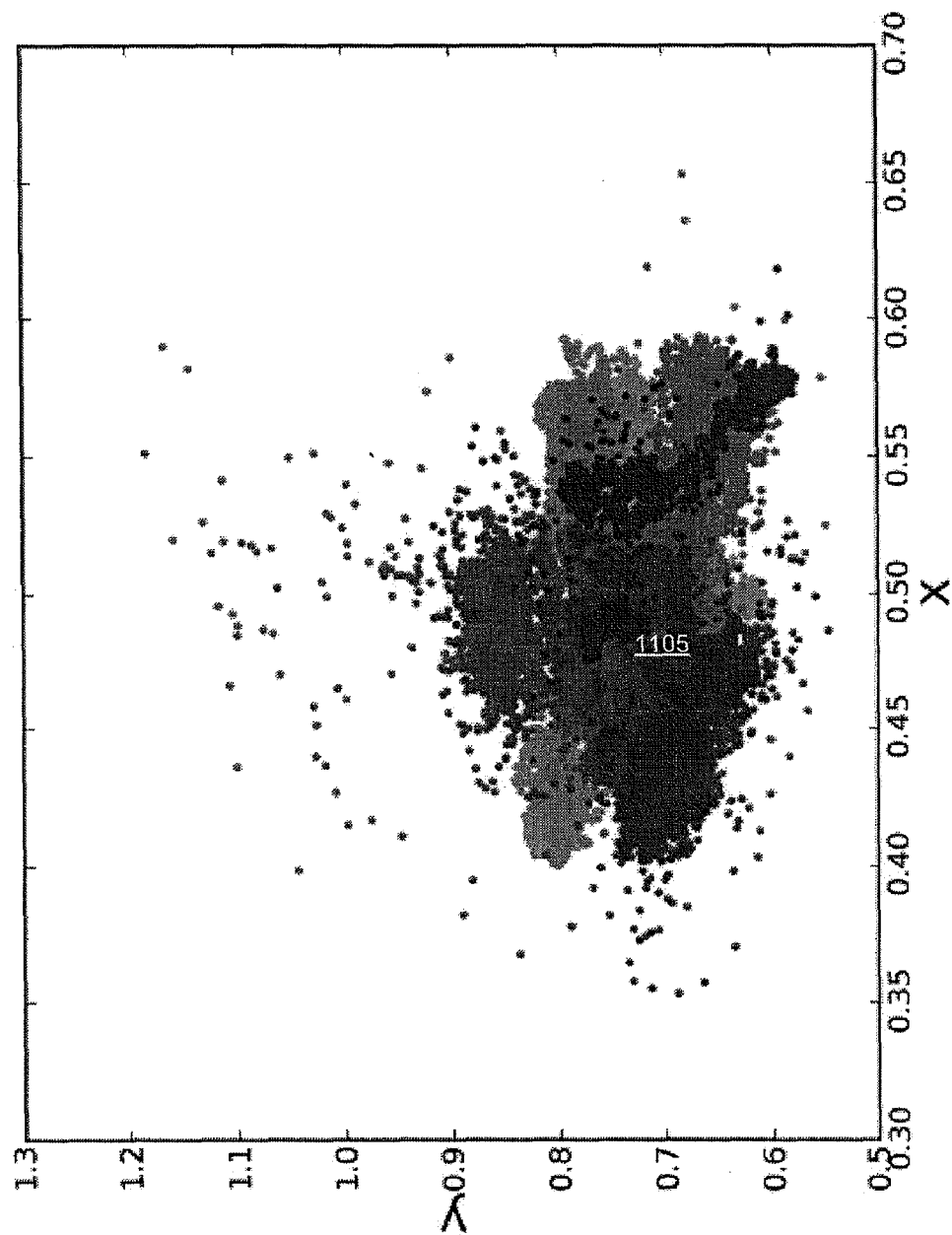
FIG. 11 is an exemplary chart illustrating a safe zone, according to an illustrative embodiment of the invention.

FIG. 11 illustrates an exemplary safe zone based on pressure points acquired from a sensor (e.g., sensor from the shoe, walker, prosthetic leg, walking aid, portion of a robotic device or other load bearing structure as described herein), according to an illustrative embodiment. In this example, the sensor was located on a shoe worn by a person/subject. Eighteen subjects stood for two intervals of two minutes each on an EquiTest platform. Weight distribution from left foot (0.0) to right foot (1.0) is shown on the x-axis. Center-of-force in the anterior (1.0) to posterior (0.0) direction is plotted on the y-axis, normalized by foot length. The different shadings correspond to different individuals. In FIG. 11, the safe zone 1105 is elliptical in shape, but is far larger than the region encompassed by a single equilibrium or any two minute standing interval. The range of pressures collected from the eighteen subjects can be utilized to create a predetermined range of postural stability. For example, people with the same characteristics (e.g., age, height, weight) as the eighteen subjects receive the predetermined range of postural stability preprogrammed into their stability processing module.

Figure 12:
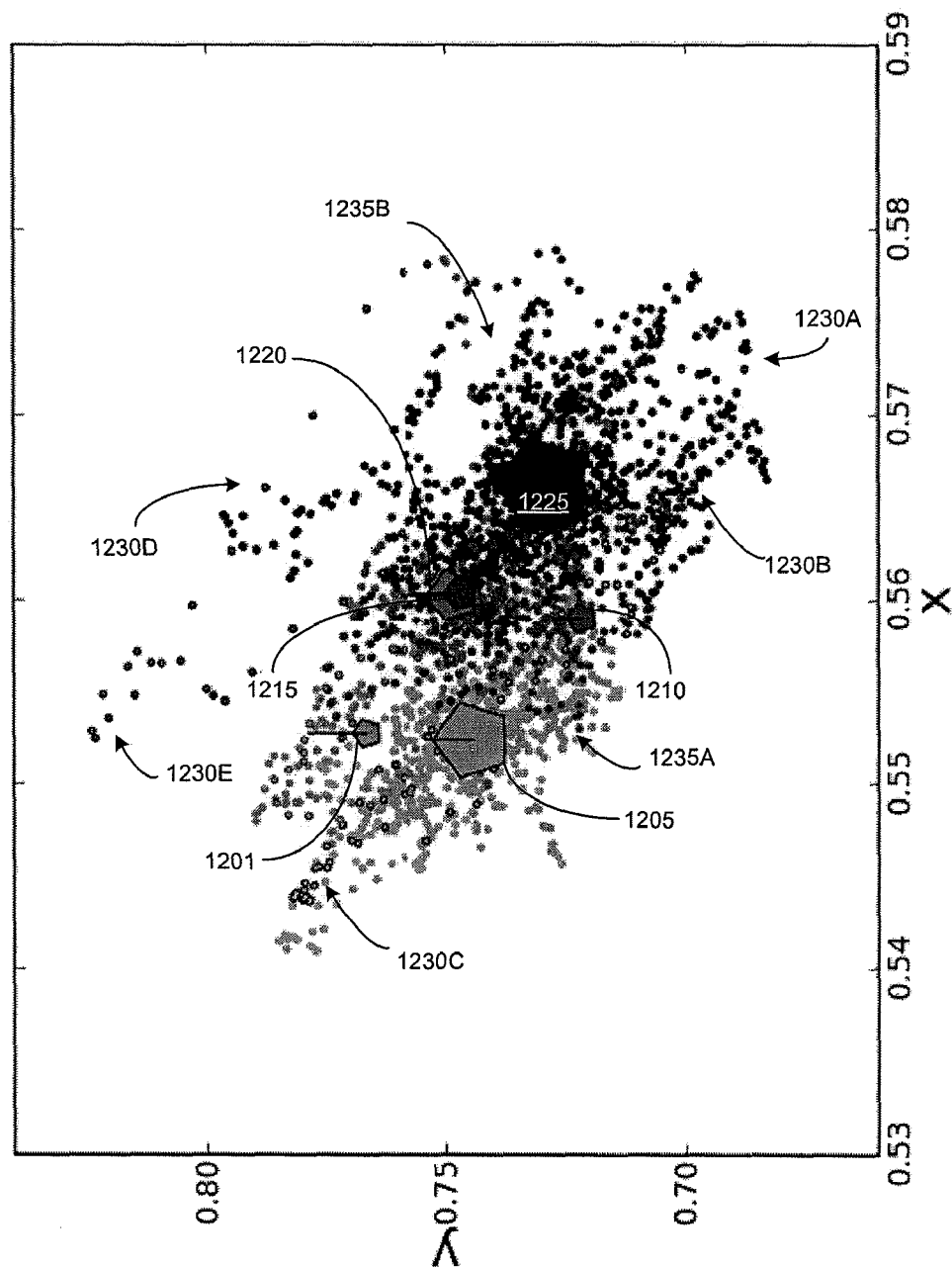
FIG. 12 is an exemplary chart illustrating equilibrium, according to an illustrative embodiment of the invention.

FIG. 12 illustrates an exemplary punctuated equilibrium during quiescent standing with eyes closed based on pressure points acquired from a sensor (e.g., sensor from the shoe, walker, prosthetic leg, walking aid, portion of a robotic device or other load bearing structure as described herein), according to an illustrative embodiment. In this example, the sensor was located on a shoe worn by a person/subject. The subject stood for two minutes on an EquiTest platform. Pressure was sampled at the right toe, the right heel, the left toe, and the left heel, at a rate of one hundred Hz. The sensor data was classified by the HMM. Center-of-force from left foot (0.0) to right foot (1.0) is shown on the x-axis. Center-of-force in the anterior (1.0) to posterior (0.0) direction was plotted on the y-axis, normalized by foot length. Earlier to later equilibria 1201, 1205, 1210, 1215, 1220 and 1225 are illustrated by the different shadings/regions (i.e., as indicated by lighter shading to dark shading). Pentagons were used to mark the center-of-force of each equilibrium. Pentagon size can correspond to dwell time. The length of the embedded line can be the average distance of each point in the equilibrium from the equilibrium center-of-mass, a measure of the compactness of the equilibrium. Dynamic trajectories (e.g., trajectories 1230A-E) that can revert to the equilibrium are bordered in a dark border. Trajectories which lead to escape from the equilibrium (e.g., trajectories 1235A-B) are bordered by a light border. In this case, the subject in this example oscillated through six equilibria 1201, 1205, 1210, 1215, 1220 and 1225 in two minutes.

Figure 13:
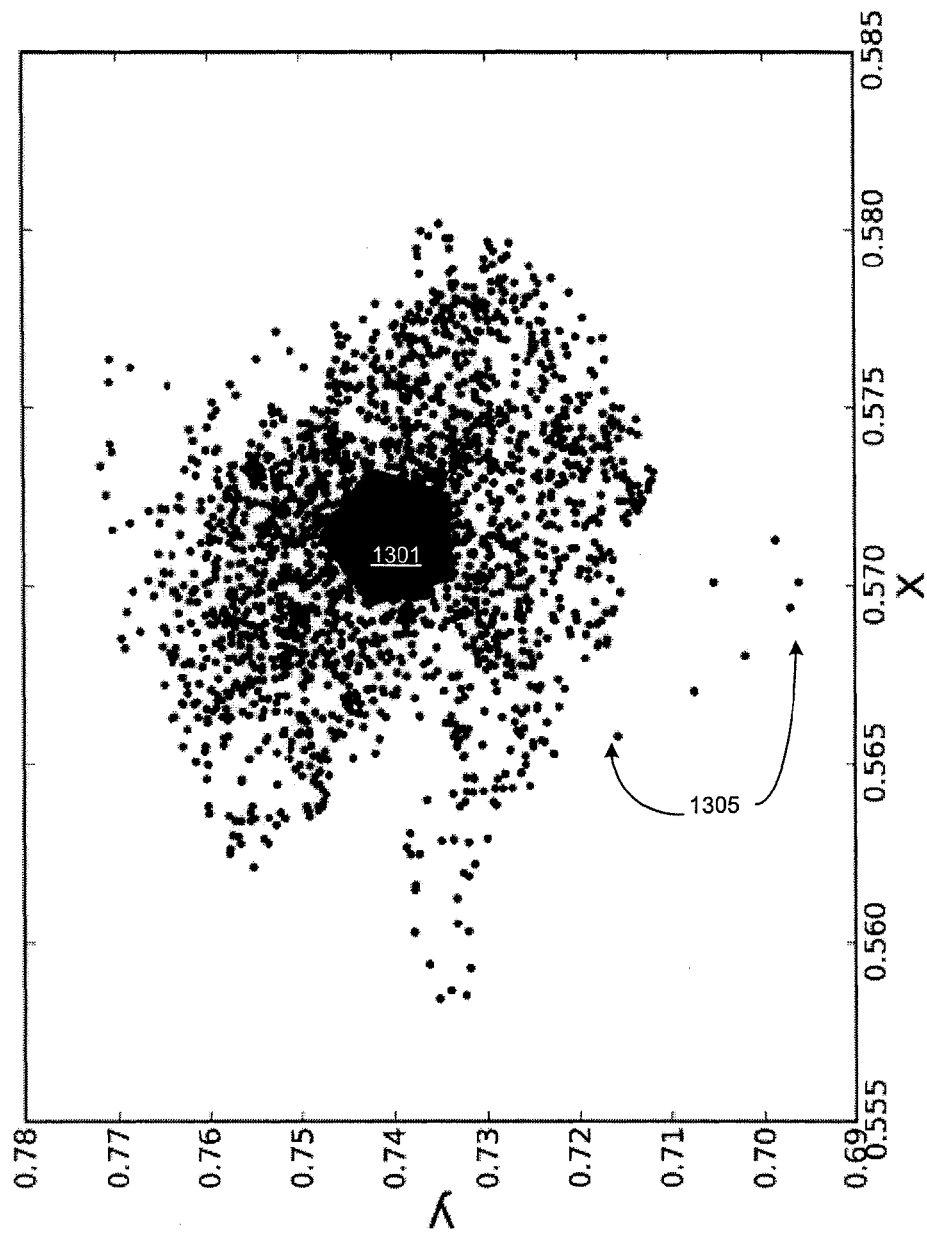
FIG. 13 is an exemplary chart illustrating equilibrium, according to an illustrative embodiment of the invention.

FIG. 13 illustrates an exemplary punctuated equilibrium during quiescent standing with eyes open based on pressure points acquired from a sensor (e.g., sensor from the shoe, walker, prosthetic leg, walking aid, portion of a robotic device or other load bearing structure as described herein), according to an illustrative embodiment. In this example, the sensor was located on a shoe worn by a person/subject. The same subject as in FIG. 12 stood for two minutes on an EquiTest platform, this time with eyes open. Pressure was sampled at the right toe, the right heel, the left toe, and the left heel, at a rate of one hundred Hz. The sensor data was classified by the HMM. Center-of-force from left foot (0.0) to right foot (1.0) is shown on the x-axis. Center-of-force in the anterior (1.0) to posterior (0.0) direction is plotted on the y-axis, normalized by foot length. A single equilibrium 1301 is seen. A dynamic trajectory 1305 (e.g., as indicated by dark border) roughly midway through the protocol ultimately reverts to the equilibrium. When eyes are open, visual feedback can enable greater stability.

Figure 14:
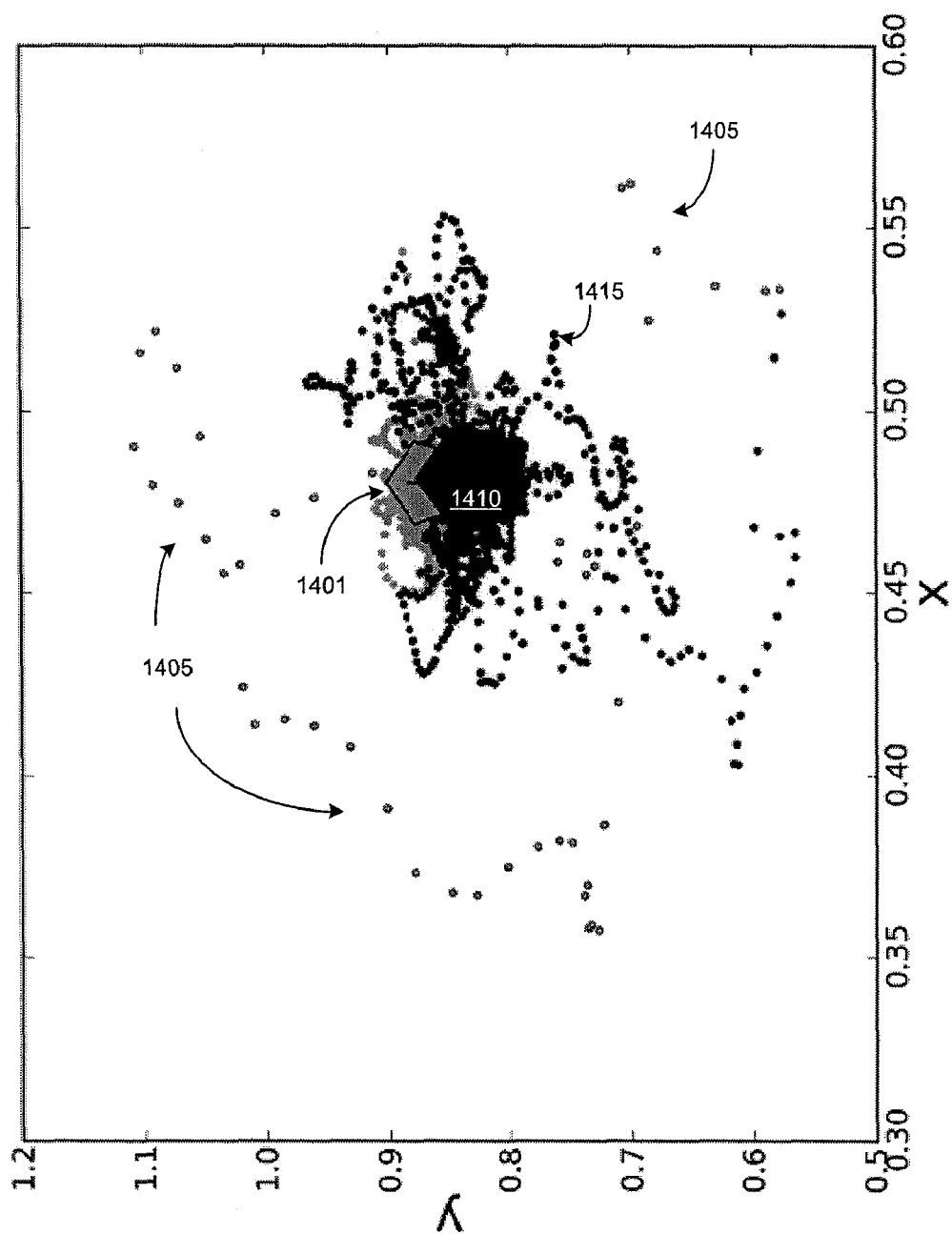
FIG. 14 is an exemplary chart illustrating equilibrium, according to an illustrative embodiment of the invention.

FIG. 14 illustrates an exemplary punctuated equilibrium during perturbed standing based on pressure points acquired from a sensor (e.g., sensor from the shoe, walker, prosthetic leg, walking aid, portion of a robotic device or other load bearing structure as described herein), according to an illustrative embodiment. In this example, the sensor was located on a shoe worn by a person/subject. The subject stood for two minutes on an EquiTest platform, squatting after forty seconds and lifting arms after eighty seconds. Pressure was sampled at the right toe, the right heel, the left toe, and the left heel, at a rate of one hundred Hz. The sensor data was classified by a Hidden Markov Model. Center-of-force from left foot (0.0) to right foot (1.0) is shown on the x-axis. Center-of-force in the anterior (1.0) to posterior (0.0) direction is plotted on the y-axis, normalized by foot length. The subject entered an initial equilibrium 1401 for forty seconds (e.g., as indicated by the lighter shading and pentagon with lighter shading), which was abruptly interrupted by a squat 1405

(e.g., as indicated by lighter shading with light border). This led into a new equilibrium 1410 (e.g., as indicated by dark shading and pentagon with dark shading). The arm lift 1415 (e.g., as indicated by dark shading with dark border) did not lead to deterioration of the equilibrium. The HMM was able to effectively identify both the squat and the arm-lift.

In some embodiments, the range of postural stability is determined by quantifying the dwell time, the size, the shape of the equilibrium, the dynamic trajectories, and/or the zone of stable equilibrium. FIGS. 10 through 14 illustrate exemplary dwell time, size, shape of equilibrium, dynamic trajectories, and zone of stable equilibrium that can be utilized to determine the range of postural stability of a subject/person.

Although the figures and examples described herein illustrate people and robots, the input sensors (e.g., 120) can be coupled to any type of load bearing structure associated with a structure. Based on the sensor information, the postural states can be determined for the structure. The structure can be, for example, a vehicle, a person, a robot, and/or any other type of structure associated with a load bearing structure. The load bearing structure can be, for example, a leg, a walking aid, an axle couple to one or more wheels, and/or any other type of structure that is load bearing.

Figure 15A:
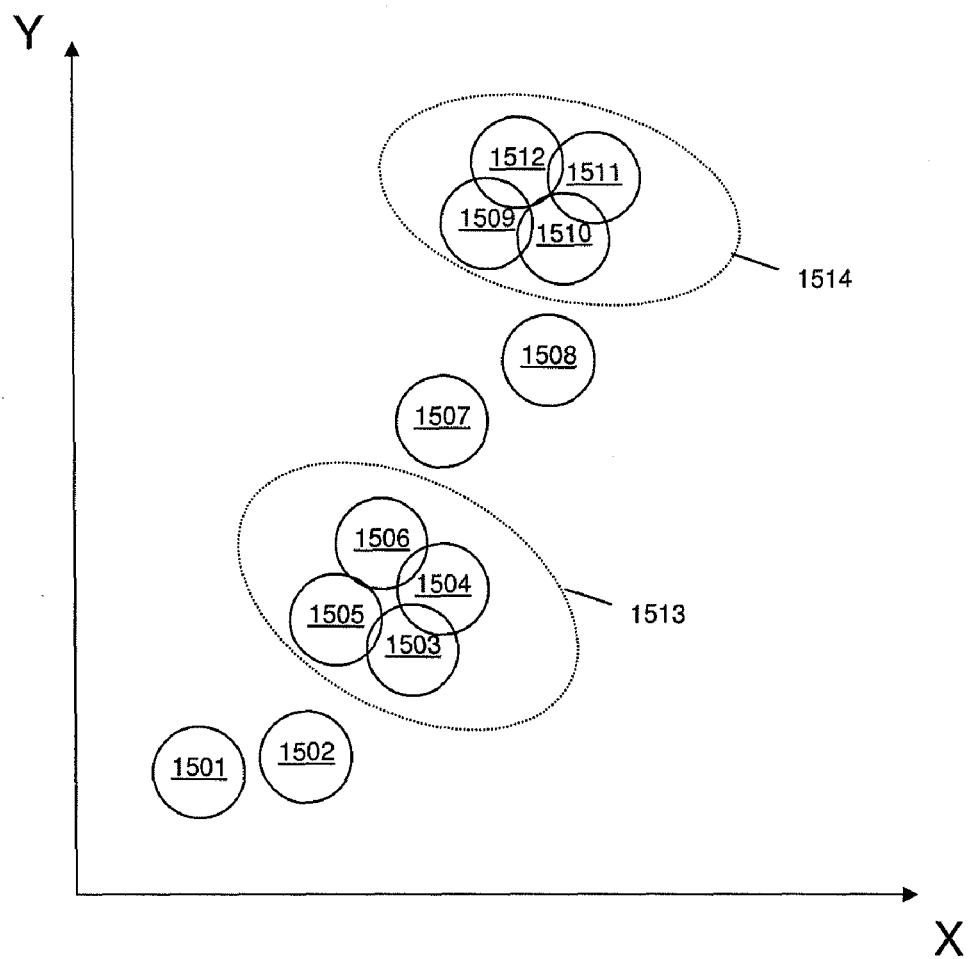
FIG. 15A is an exemplary illustration of data acquired from a pressure sensor, according to an illustrative embodiment of the invention.
Figure 15B:
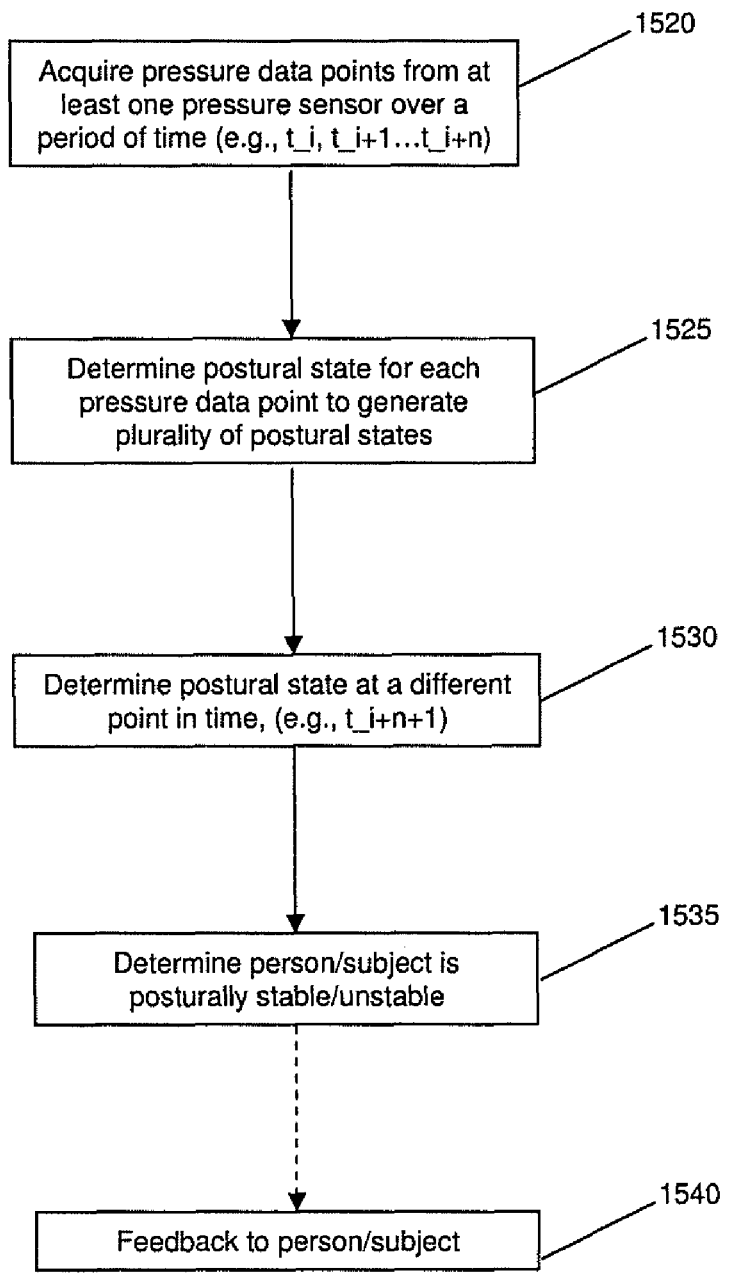
FIG. 15B illustrates a method for determining postural stability of a person based on the exemplary illustration of the data from FIG. 15A, according to an illustrative embodiment of the invention.

FIG. 15A illustrates data acquired from at least one pressure sensor over time, according to an illustrative embodiment. FIG. 15B illustrates a method for determining postural stability of a person based on the data acquired from the pressure sensor, according to an illustrative embodiment of the invention. Pressure data points 1501-1512 can be acquired from a sensor (e.g., sensor/input sensor from a shoe worn by the person, a walker, a prosthetic leg, walking aid, portion of a robotic device or other load bearing structure as described herein). The x-axis and the y-axis can correspond to locations of the pressure data points. For example, in the case where a pressure sensor is located on a shoe worn by a person/subject, then the x-axis can represent the lateral locations (e.g., right and left foot) on the person and the y-axis can represent fore-aft locations (e.g., toe and heel) on the person's foot.

A method for determining postural stability (e.g., of a person or a robot or vehicle, etc.) can include acquiring a plurality of pressure data points (e.g., pressure data points 1501-1512) over a period of time (e.g., at time t_i, t_i+1 ... t_i+n) from at least one pressure sensor (step 1520). A postural state can be identified for each pressure data point to generate a plurality of postural states (e.g., which can include a range of postural states) (step 1525). A postural state of a person (e.g., or other load bearing structure) at a point in time can be determined based on at least the plurality of postural states (step 1530). In some embodiments, the postural state a point in time is the subsequent postural state of the person (e.g., at time t_i+n+1). In some embodiments, the postural state of the person is determined at a later point in time, t_i+n+m where m is a value corresponding to how much time has lapsed between when the pressure data points were acquired to when the data points are analyzed to determine the postural state. In some embodiments, a person can be identified as posturally stable or unstable based on the data points/postural states (step 1535).

A method for determining postural stability (e.g., stability of a person) can also include the step of acquiring at least a first pressure data point and a second pressure data point from at least one pressure sensor (e.g., sensor/input sensor from the shoe, walker, prosthetic leg, walking aid, portion of a robotic device or other load bearing structure as described herein). The first pressure data point can correspond to pressure data point 1501 and the second pressure data point can be 1502. The method can also include identifying a first postural state and a second postural state based on the first and second pressure data points 1501 and 1502. The first and second postural states can be individually identified as static or dynamic. The method can also include determining a postural state (e.g., of the person) at a point in time (e.g., a subsequent postural state or a postural state of a person at a later point in time after the data points have been acquired) based on at least the first postural state and the second postural state. For example, person can be identified as posturally stable or unstable based on at least the identified first postural state and the identified second postural state (e.g., step 1535).

The step (e.g., step 1525 from FIG. 15B) of identifying/determining a postural state for each corresponding pressure data point (e.g., any one of pressure data points 1501-1512 from FIG. 15A) can generate a plurality of postural states. A range of postural stability can be determined based on the plurality of pressure data points or the corresponding plurality of postural states (e.g. from step 1525 from FIG. 15B).

In some embodiments, the postural state identified for each pressure data points (e.g., any one of pressure data points 1501-1512 from FIG. 15A) can be identified as a static postural state or a dynamic postural state. A dynamic postural state can be defined as when the person is moving between static postural states (e.g., moving from a first static postural state to a second static postural state). By way of example, in FIG. 15A, pressure data points 1503-1506 and pressure data points 1509-1512 can be each identified as static postural states and pressure data points 1501-1502 and pressure data points 1507-1508 can be each identified as dynamic postural states.

Threshold functions can be performed on the pressure data points (e.g., pressure data points 1501-1512 from FIG. 15A). A person can be determined or identified as being posturally stable or posturally unstable (e.g., step 1535 from FIG. 15B) based on a number of times the person is in the dynamic postural state. For example, if the number of times the person transitions from a static postural state to a dynamic postural state exceeds a predetermined threshold, then the person can be identified as being posturally unstable.

In some embodiments, data points (e.g., pressure data points 1501-1512 from FIG. 15A) from input sensors (e.g., pressure sensors) can be processed to determine if a condition occurs. For example, a rule can include measuring an average velocity (e.g., of a person or other load bearing structure) over a period/window of time. In some embodiments, the rule or condition used to assess/determine postural stability can be based on the number of velocity related emission states out of a number of points/periods of time (e.g., whether there are more than 100 high-velocity emission states out of 150 time periods, etc). In some embodiments, the rules based methods do not use the number of dynamic states to determine a person's overall postural state (e.g., determining the postural stability). A simple thresholding algorithm can take the outputs themselves, (e.g., such as the velocity of a person) in either a binned form (e.g., in the emission matrix) or unbinned form.

In some embodiments, the plurality of postural states based on the pressure data points 1501-1512 follows a punctuated equilibrium (e.g., as described in FIG. 14). A continuous series of static postural states can define an equilibrium. By way of example, each of the plurality of pressure data points 1501-1512 can correspond to the following exemplary/illustrative sequence of postural states, where "S" corresponds to a static postural state and "D" corresponds to a dynamic postural state: D (e.g., data point 1501), D (e.g., data point 1502), S (e.g., data point 1503), S (e.g., data point 1504), S (e.g., data point 1505), S (e.g., data point 1506), D (e.g., data point 1507), D (e.g., data point 1508), S (e.g., data point 1509), S (e.g., data point 1510), S (e.g., data point 1511), S (e.g., data point 1512), etc. A series of static postural states (e.g., and corresponding pressure data points 1503-1506 and 1509-1512) can be grouped together to define an equilibrium 1513 or 1514. A person can be determined/identified as being posturally stable or posturally unstable (e.g., step 1535 from FIG. 15B) based on a number of distinct equilibria 1513 and 1514. By way of example, if the number of distinct equilibria (e.g., the number of series/groups of static postural states) exceeds a certain threshold, then the person can be identified as being posturally unstable.

The "postural state of the person at a point in time" (e.g., step 1530 from FIG. 15B) can be defined, for example, as a past postural state of the person, a current postural state of the person or a subsequent postural state of the person. Any one of a past postural state, current postural state or a subsequent postural state of the person can be determined by looking at or analyzing the plurality of pressure data points 1501-1512 acquired from pressure sensor.

In some embodiments, the postural state of the person at a point in time (e.g., step 1530 from FIG. 15B) can be calculated or determined in real time as the pressure data points 1501-1512 are being acquired by a sensor. Pressure data points 1501-1512 can represent a postural state of the position at each point in time during an acquisition period (e.g., step 1520 from FIG. 15B). For example, pressure data points 1501-1512 can represent pressure data points at times t_1, t_2, t_3 . . . t_12, where points of time t_1 through t_12 can define a data acquisition period of time. If the postural state of a person at a point in time is calculated in real time, pressure data points 1501-1512 can be acquired and a postural state of the person at time t_13, etc. (e.g., a subsequent postural state), etc. can be calculated.

In some embodiments, pressure data points 1501-1512 can be acquired over a period of time and later used to calculate a postural state of the person at a later point in time (e.g., 6 months later). For example, as stated above, pressure data points 1501-1512 from FIG. 15A can represent pressure data points at times t_1, t_2, t_3 . . . t_12. By way of example, pressure data points 1501-1512 can later be used for diagnostic purposes or analyzed at a later point in time to project what the current postural state of the person is and what a subsequent postural state of the person might be. For example, pressure data points 1501-1512 acquired during times t_1, t_2, t_3 . . . t_12 can be used at a later point in time (e.g., time point t_50) to determine a current postural state (e.g., at time point t_50), a previous postural state (e.g., at time point t_49) or subsequent postural state (e.g., at time point t_51).

In some embodiments, a Hidden Markov Model can be used to calculate a postural state of the person (e.g., step 1530 from FIG. 15B) at a point in time (e.g., a past postural state, current postural state or subsequent postural state of the person). For example, pressure data points (e.g., data points 1501-1512 from FIG. 15A) can be used in a Hidden Markov Model to calculate a subsequent postural state of a person. Each pressure data point 1501-1512 can be identified as type of postural state (e.g., static postural state or dynamic postural state) (e.g., step 1525 from FIG. 15B). Pressure data points 1501-1512 can be acquired over a period of time (e.g., acquisition period at time points t_1, t_2, t_3 . . . t_12, for example, in step 1520 in FIG. 15B). The range of postural states (e.g., the sequence of postural states generated from pressure data points 1501-1512), a probability of transitioning between the types of postural states (e.g., probability of transitioning between static state or dynamic state) and a current postural sate (e.g., postural state at time point t_12) can be used in a Hidden Markov Model to determine a subsequent postural state (e.g., a postural state at time point t_13). A Hidden Markov Model can be used to determine a past or a present postural state (e.g., a postural state at time point t_11 or t_12).

In some embodiments, a Bayesian segmentation can be applied to the plurality of pressure data points (e.g., corresponding to pressure data points 1501-1512 from FIG. 15A and determined, for example, at step 1525 from FIG. 15B) to determine a postural state of a person at a point in time.

In some embodiments, the postural state of the person at a point in time (e.g., a subsequent postural state of the person) (step 1530) is determined or calculated based on at least probability of transitioning between the static postural state and the dynamic postural state. The probability of transitioning between states can be calculated based on the plurality of postural states of the person over the period of time (e.g., over an acquisition period). For example, the probability of transitioning between states can be determined by looking at the postural states that correspond to the pressure data points 1501-1512 that were acquired from the sensor (e.g., by looking at how the sequence of the postural states varies over time) in step 1530 of FIG. 15B. By way of example, if pressure data points 1501-1512 correspond to the following sequence of postural states: D, D, S, S, S, S, D, D, S, S, S, S where "D" is a dynamic state and "S" is a static state, then any portion or all of the sequence can be used to calculate/determine a probability of transitioning between the static postural state and the dynamic postural state.

In some embodiments, each of the plurality of pressure data points 1501-1512 from FIG. 15A reflects a location of a center of mass of the person at a point in time. For example, if the sensor is on a shoe worn by a person, as the person is shifting/moving/swaying, the center of mass/gravity/force of the person can move as well. In some embodiments, a change of the location of the center of mass of the person over the period of time is determined based on the plurality of pressure data points 1501-1512. A selected set of the plurality of pressure data points can be grouped (e.g., groups 1513 or 1514) as corresponding to a static or dynamic postural state of the person. The selected set of the plurality of pressure data points can be grouped based on the corresponding location of center of mass/gravity/force. For example, pressure data points 1503-1506 and 1509-1912 can indicate that the person's center of mass/gravity/force has remained relatively stable (e.g., a static postural state) because the location of the center of mass has not changed relative to the other data points. However, pressure data points 1501, 1502, 1507 and 1508 can indicate that the location of the person's center of mass/gravity/force is changing (e.g., a dynamic postural state).

In some embodiments, a person's activity can be monitored in addition to acquiring pressure sensor information. For example, an acceleration of a person over time can be acquired (e.g., by use of a measurement device such as an accelerometer). In some embodiments, a location of the person can also be acquired (e.g., by using a GPS device). Information regarding a person's activity can be used, for example, for diagnostic purposes.

In some embodiments, the pressure data points 1501-1512 (e.g., information acquired from pressure sensors on a load bearing structure as described herein) can be analyzed using, for example, Fourier transform or other signal processing techniques. In some embodiments, the pressure data points can be analyzed to determine if there is a periodicity to the data (e.g., pressure data points 1501-1512 from FIG. 15A). A periodicity of the pressure data points can be used in connection with biometric data (e.g., heart rate, breathing, etc.) and can be used for diagnostic purposes.

The above-described embodiments, methods and systems can also be used in connection with feedback (e.g., immediate feedback). By way of example, feedback (e.g., real-time or immediate) can be used to alert a person or a load bearing structure as described herein (e.g., robot, vehicle, etc.) The feedback could be used in connection with the determined postural stability (e.g., to alert the person that they are or will be posturally unstable) (e.g., step 1540 of FIG. 15B). By way of example, feedback could be accomplished via vibration (e.g., stimulation or vibration at feet or elsewhere), via vision (e.g., presenting the pressure data to the person's visual field, either on a phone, special glasses, or modified contact lenses), via hearing (e.g., head-phones or bone-phones) via taste (using some sort of cartridge in the person's mouth), via temperature (e.g., at feet or elsewhere), via other sensory mechanisms (e.g., a tactile mechanism), or any combination thereof. This feedback could be used to improve balance or in connection with balance training or physical therapy, etc.

Figure 16:
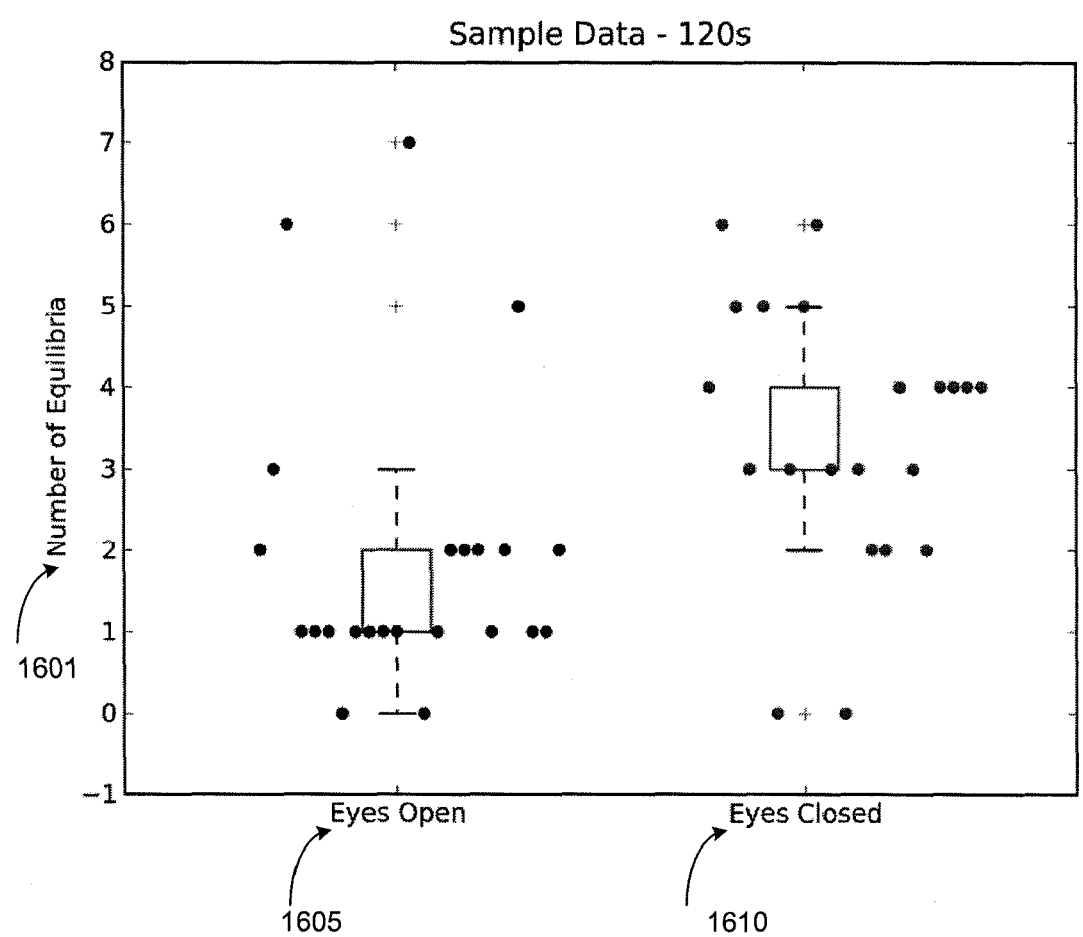
FIG. 16 is an illustrative graph comparing the number of equilibria from subjects.

FIG. 16 is an illustrative graph comparing the number of equilibria 1600 from subjects. Data (e.g., such as data described above in FIGS. 10-14 taken from input sensors) taken from subjects with their eyes open 1605 and subjects with their eyes closed 1610. As shown in the graph, the number of equilibria (e.g., equilibria as described above in FIGS. 10-14) increased when the subjects had their eyes closed (i.e. which could lead to imbalance/postural instability) as compared to when the subjects had their eyes opened.

The above-described systems and methods can be implemented in digital electronic circuitry, in computer hardware, firmware, and/or software. The implementation can be as a computer program product. The implementation can, for example, be in a machine-readable storage device, for execution by, or to control the operation of, data processing apparatus. The implementation can, for example, be a programmable processor, a computer, and/or multiple computers.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by and an apparatus can be implemented as special purpose logic circuitry. The circuitry can, for example, be a FPGA (field programmable gate array) and/or an ASIC (application specific integrated circuit). Modules, subroutines, and software agents can refer to portions of the computer program, the processor, the special circuitry, software, and/or hardware that implements that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magneto-optical disks, or optical disks).

Data transmission and instructions can also occur over a communications network. Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above described techniques can be implemented on a computer having a display device. The display device can, for example, be a cathode ray tube (CRT) and/or a liquid crystal display (LCD) monitor. The interaction with a user can, for example, be a display of information to the user and a keyboard and a pointing device (e.g., a mouse or a trackball) by which the user can provide input to the computer (e.g., interact with a user interface element). Other kinds of devices can be used to provide for interaction with a user. Other devices can, for example, be feedback provided to the user in any form of sensory feedback (e.g., visual feedback, auditory feedback, or tactile feedback). Input from the user can, for example, be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, wireless networks, a packet-based network, and/or a circuit-based network.

Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), 802.11 network, 802.16 network, general packet radio service (GPRS) network, HiperLAN), and/or other packet-based networks. Circuit-based networks can include, for example, the public switched telephone network (PSTN), a private branch exchange (PBX), a wireless network (e.g., RAN, bluetooth, code-division multiple access (CDMA) network, time division multiple access (TDMA) network, global system for mobile communications (GSM) network), and/or other circuit-based networks.

The system can include clients and servers. A client and a server are generally remote from each other and typically interact through a communication network. The relationship of client and server arises by virtue of computer programs running on the respective computers and having a client-server relationship to each other.

The handheld device can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a world wide web browser (e.g., Microsoft® Internet Explorer® available from Microsoft Corporation, Mozilla® Firefox available from Mozilla Corporation). The mobile computing device includes, for example, a personal digital assistant (PDA).

Comprise, include, and/or plural forms of each are open ended and include the listed parts and can include additional parts that are not listed. And/or is open ended and includes one or more of the listed parts and combinations of the listed parts.

While this invention has been particularly shown and described with references to preferred embodiments thereof, it will be understood by those skilled in the art that various changes in form and details may be made therein without departing from the scope of the invention encompassed by the appended claims.

What is claimed is:

1. A computer-implemented method for determining postural stability of a person, the method comprising:
    acquiring, by a processor, a plurality of pressure data points over a period of time from at least one pressure sensor;
    identifying, by the processor, a postural state for each pressure data point to generate a plurality of postural states; and
    determining, by the processor, a postural state of the person at a point in time based on at least the plurality of postural states and a probability of transitioning between at least one of the plurality of postural states and another postural state, wherein the postural state is at least one of a static postural state or a dynamic postural state.

2. The method of claim 1, wherein the person is in the dynamic postural state when moving from a first static postural state to a second static postural state.

3. The method of claim 1, further comprising determining that the person is posturally stable or posturally unstable based on a number of times the person is in the dynamic postural state.

4. The method of claim 1, wherein the plurality of postural states follows a punctuated equilibrium, a continuous series of static postural states defining an equilibrium.

5. The method of claim 4, further comprising determining that the person is posturally stable or posturally unstable based on a number of distinct equilibria.

6. The method of claim 1, wherein determining the postural state of the person at the point in time is based on at least a probability of transitioning between the static postural state and the dynamic postural state.

7. The method of claim 6, further comprising calculating the probability of transitioning between the static postural state and the dynamic postural state based on the plurality of postural states of the person over the period of time.

8. The method of claim 1, further comprising acquiring at least one of an acceleration or a location of the person over the period of time.

9. The method of claim 1, further comprising determining a range of postural stability states based on the plurality of pressure data points.

10. The method of claim 1, wherein determining comprises using a machine learning technique on the plurality of pressure data points to generate the plurality of postural states.

11. The method of claim 10, wherein determining comprises using a Hidden Markov Model on the plurality of pressure data points or applying Bayesian segmentation to the plurality of pressure data points to generate the plurality of postural states.

12. The method of claim 1, wherein acquiring comprises acquiring a plurality of pressure data points from at least one pressure sensor on at least one of a shoe, a sock, a sole insert, a cane, a crutch, a walker, a walking aid, a prosthetic leg, or a robotic leg.

13. The method of claim 1, wherein each of the plurality of pressure data points reflects a location of a center of mass of the person at a point in time.

14. The method of claim 13, wherein identifying comprises grouping a selected set of the plurality of pressure data points as corresponding to a static postural state based on the location of the center of mass of the person of each of the plurality of pressure data points.

15. The method of claim 1, wherein determining comprises determining in real time, a subsequent postural state of the person based on the plurality of pressure data points.

16. The method of claim 1, wherein determining comprises determining a current postural state or a subsequent postural state of the person based on the plurality of pressure data points, wherein the plurality of pressure data points were acquired during a previous period in time.

17. A computer-implemented method for determining postural stability, the method comprising:
    acquiring, by a processor, at least a first pressure data point and a second pressure data point from at least one pressure sensor;
    identifying, by the processor, a first postural state and a second postural state based on the first and second pressure data points, wherein identifying comprises identifying the first postural state as static or dynamic and the second postural state as static or dynamic; and
    determining, by the processor, a postural state at a point in time based on at least the first postural state, the second postural state, and a probability of transitioning between at least one of the first or second postural states and another postural state.

18. The method of claim 17, wherein determining comprises determining a subsequent postural state of a person.

19. The method of claim 17, wherein determining comprises determining a subsequent postural state of a person based on a probability of transitioning between the static postural state and the dynamic postural state.

20. The method of claim 17, further comprising determining that a person is posturally stable or posturally unstable based on at least the identified first postural state and the identified second postural state.

21. The method of claim 17, wherein acquiring comprises acquiring a plurality of pressure data points from at least one pressure sensor on at least one of a shoe, a sock, a sole insert, a cane, a crutch, a walker, a walking aid, a prosthetic leg, a robotic leg, a vehicle, or an axle connected to at least one wheel.

22. A system for determining postural stability of a person comprising:
    at least one pressure sensor coupled to the person that acquires a plurality of pressure data points over a period of time;
    means for identifying a postural state for each pressure data point;
    means for generating a plurality of postural states of the person over the period of time; and means for determining a postural state of the person at a point in time based on the plurality of postural states and a probability of transitioning between at least one of the plurality of postural states and another postural state, wherein the postural state of the person is one of a static postural state or a dynamic postural state.

23. The system of claim 22, wherein each pressure data point corresponds to a center of gravity of the person at a point in time.

* * * * *